US005665550A

United States Patent [19]
Roninson et al.

[11] Patent Number: 5,665,550
[45] Date of Patent: Sep. 9, 1997

[54] GENES AND GENETIC ELEMENTS ASSOCIATED WITH SENSITIVITY TO CHEMOTHERAPEUTIC DRUGS

[75] Inventors: Igor B. Roninson, Wilmette; Andrei Gudkov, Chicago, both of Ill.

[73] Assignee: Board of Trustees of the University of Illinois-Urbana, Chicago, Ill.

[21] Appl. No.: 480,552

[22] Filed: Jun. 7, 1995

Related U.S. Application Data

[63] Continuation of Ser. No. 33,086, filed as PCT/US91/07492, Oct. 11, 1991 published as WO92/0701, Apr. 30, 1992, abandoned, which is a continuation-in-part of Ser. No. 599,730, Oct. 19, 1990, Pat. No. 5,217,889.

[51] Int. Cl.$^6$ .............................. C12Q 1/68; C12P 21/02
[52] U.S. Cl. .......................... 435/6; 435/69.1; 435/172.3; 435/91.41; 435/252.33; 435/325; 435/357; 435/367; 435/372; 536/23.1; 536/23.4; 536/24.5
[58] Field of Search .................... 435/6, 172.3, 91.41, 435/240.2, 252.33, 320.1, 69.1; 536/23.4, 23.5, 24.3, 24.5, 25.3

[56] References Cited

U.S. PATENT DOCUMENTS 5,217,889  6/1993  Roninson et al. .................... 435/172.3

FOREIGN PATENT DOCUMENTS

WO8803558  5/1988  WIPO.

OTHER PUBLICATIONS

Sczakielet al., 1990, "Specific inhibition of human immunodeficiency virus type 1 replication by RNA transcribed in sense and antisense orientation from the 5'–leader/gag region," *Biochem. Biophys. Res. Commun.* 169: 643–651.

Friedman et al., 1988, "Expression of a truncated viral trans–activator selectively impedes lytic infection by its cognate virus", *Nature* 335: 452–454.

Napoli et al., 1990, "Introduction of a chimeric chalcon synthase gene into petunia results in reversible co–suppression of homologous genes in trans," *The Plant Cell* 2: 279–289.

Kidd et al., 1989, "Dominant negative mutation in galactosyl transferase created by over–expression of a truncated cDNA," *Gene Transfer & Gene Therapy* pp. 225–234.

Baird et al., 1990, "Identification, cloning, and characterization of the *Escherichia coli* sohA gene, a suppressor of the htrA(degP) null phenotype," *J. Bacteriol.* 172: 1587–1594.

Kosik et al., 1990, "The primary structure and analysis of the squid kinesin heavy chain," *J. Biol. Chem.* 265: 3278–3283.

Ferreira et al., 1992, "Suppression of kinesin expression in cultured hippocampal neurons using antisense oligonucleotides," *J. Cell. Biol.* 117: 595–606.

Chen et al., 1986, "Internal Duplication and Homology with Bacterial Transport Proteins in the mdr1 (P–Glycoprotein) Gene from Multidrug–Resistant Human Cells", *Cell* 47: 381–389.

Noonan et al., 1990, "Quantitative analysis of MDR1 (multidrug resistance) gene expression in human tumors by polymerase chain reaction", *Proc. Natl. Acad. Sci. USA* 87: 7160–7164.

Holzmayer et al., 1992, "Isolation of dominant negative mutants and inhibitory antisense RNA sequences by expression selection of random DNA fragments", *Nucleic Acids. Res.* 20: 711–717.

Culver et al., 1992, "In Vivo gene Transfer with Retroviral Vector–Producer Cels for Treatment of Experimental Brain Tumors", *Science* 256: 1550–1552.

Gudkov et al., 1993, "Isolation of genetic suppressor elements, inducing resistance to topoisomerase II–interactive cytotoxic drugs, from human topoisomerase II cDNA", *Proc. Natl. Acad. Sci. USA* 90: 3231–3235.

Groger et al. (1989) *Gene* 81, 285–294.

Lock et al. (1988) *Int. J. Cancer* 42(3), 371–381.

Patanjali et al. (1991) *PNAS USA* 88, 1943–1947.

Shen et al. (1986) *Science* 232, 643–645.

Tsai–Pflugfelder et al. (1988) *PNAS USA* 85, 7177–7181.

Uhlmann et al. (1990). *Chem. Rev.* 90(4), 543–584.

Holzmayer et al. (1992) *Nuc. Acids Res* 20(4), 711–717.

*Primary Examiner*—James Ketter
*Attorney, Agent, or Firm*—McDonnell Boehnen

[57] ABSTRACT

The invention provides genetic suppressor elements that confer upon a cell resistance to one or more chemotherapeutic drug, methods for identifying and obtaining such elements, and methods of using such elements. The invention also provides cloned genes associated with sensitivity to chemotherapeutic drugs.

93 Claims, 42 Drawing Sheets

FIG. 1A

```
GTGTCTGGGC GGAGCAAAAT ATGTTCCAAT TGTGTTTTCT TTTGATAGAT TCTTTCAACA     60
GACAGTCTTT TCTTAGCATC TTCATTTTTC TTTATTTTGT TGACTTGCAT ATTTTCATTT    120
ACAGGCTGCA ATGGTGACAC TTCCATGGTG ACGGTCGTGA AGGG                     164
```

FIG. 1B

```
TGAAAAGATG TATGTCCCAG CTCTCATATT TGGACAGCTC CTAACTTCTA GTAACTATGA    60
TGATGATGAA AAGAAAGTGA CAGGTGGTCG AAATGGCTAT GGAGCCAAAT TGTGTAACAT   120
ATTCAGTACC AAATTTACTG TGGAAACAGC CAGTAGAGAA TACAAGAAAA TGTTCAAACA   180
GACATGGATG GATAATATGG GAAGAGCTGG TGA                                213
```

FIG. 1C

```
GCCCATTGGT CAGTTTGGTA CCAGGCTACA TGGTGGCAAG GATTCTGCTA GTCCACGATA    60
CATCTTTACA ATGCTCAGCT CTTTGGCTCG ATTGTTATTT CCACCAAAAG ATGATCACAC   120
GTTGAAGTTT TTATATGATG ACAACCAGCG TGTTGAGCCT GAATGGTACA TTCCTATTAT   180
T                                                                  181
```

FIG. 1D

```
TGAATGGTAC ATTCCTATTA TTCCCATGGT GCTGATAAAT GGTGCTGAAG GAATCGGTAC   60
TGGGTGGTCC TGCAAAATCC CCAACTTTGA TGTGCCGTGAA ATTGTAAATA ACATCAGGCG  120
TTTGATGGAT GGAGAAGAAC CTTTGCCAAT GCTTCCAAGT TACAAGAACT TCAAGGGTAC  180
TATTGAAGAA CTGGCTCCAA ATCAATATGT GATTAGTGGT GAAG                    224
```

FIG. 1E

```
TGCGTGAAAT TGTAAATAAC ATCAGGCGTT TGATGGATGG AGAAGAACCT TTGCCAATGC   60
TTCCAAGTTA CAAGAACTTC AAGGGTACTA TTGAAGAACT GGCTCCAAAT CAATATGTGA  120
TTAGTGGTGA AGTAGCTATT CTTAATTCTA CAACCATTGA AATCTCAGAG CTTCCCGTCA  180
GAACATGGAC CCAGACATAC AAAGAACAAG TTCTAGAACC CATGTTGAAT GGCACCGAGA  240
AGACACCTCC TCTCATAACA GACTATAGGG AATACCATAC AGATACCACT GTGAAATTTG  300
TTGTGAAGAT GACTGAAGAA AAACTGGCA                                    329
```

FIG. 1F

```
CACTCTTTTC AGTTCCTTT TCGTTGTCAC TCTCTTCATT TTCTTCTTCA TCTGGAACCT    60
TTTGCTGGGC TTCTTTCCAG GCCTTCACAG GATCCGAATC ATATCCCCTC TGAATCAGAA   120
CTTTAATTAA TTCTTTCTTA GGCTTATTTT CAATGATTAT TTTGCCATCT ATTTTCTCTA   180
AGATAAAGCG AGCC                                                     194
```

FIG. 1G

```
TCTGCCCTCTG CTTTCATTTC TATGGTTATT CGTGGAATGA CTCTTTGACC ACGCGGAGAA   60
GGCAAAACTT CAGCCATTTG TGTTTTTTTC CCCTTGGCCT TCCCCCCTTT CCCAGGAAGT  120
CCGACTTGTT CATCTTTGTTT TTCCTTGGCT TCAACAGCCT CCAATTCTTC AATAAATGTA  180
GCCAAGTCTT CTTTCCACAA ATCTGA                                       206
```

FIG. 1H

```
GACACGACAC TTTTCTGTGG TTTCAGTTCT TTGTTACTAA GTTTTGGGGA AGTTTTGGTC    60
TTAGGTGGAC TAGCATCTGA TGGGACAAAA TCTTCATCAT CAGTTTTTTC ATCAAAATCT   120
GAGAAATCTT CATCTGAATC CAAATCCATT GTGAATTTTG TTTTGTTGC TGCTCTCCGT   180
GGCTCTGTTT CTCG                                                    194
```

FIG. 11

```
CTGAAACCAC AGAAAAGTGT CGTGTCAGAC CTTGAAGCTG ATGATGTTAA GGGCAGTGTA   60
CCACTGTCTT CAAGCCCTCC TGCTACACAT TTCCCAGATG AAACTGAAAT TACAAACCCA  120
GTTCCTAAAA AGAATGTGAC AGTGAAGAAG ACAGCAGCAA AAAGTCAGTC TTCCACCTCC  180
ACTACCGGTG CCAAAAAAAG GGCTGCCCCA AAAGGAACTA AAAGGGATCC AGCTTTGAAT  240
TC                                                                 242
```

FIG. 1J

```
AATTCAAAAGC TGGATCCCTT TTAGTTCCTT TTGGGGCAGC CCTTTTTTTG GCACCGGTAG    60
TGGAGGTGGA AGACTGACTT TTTGCTGCTG TCTTCTTCAC TGTCACATTC TTTTTAGGAA   120
CTGGGTTTGT AATTTCAGTT TCATCTGGGA AATGTGTAGC AGGAGGGCTT GAAGACAGTG   180
GTACACTGCC CTTAACATCA TCAGCTTCAA GGTCTGACAC                         220
```

Figure 1K

```
AATTCAAAGC TGGATCCCTT TTAGTTCCTT TTGGGGCAGC CCTTTTTTG GCACCGGTAG    60
TGGAGGTGGA AGACTGACTT TTGCTGCTG TCTTCTTCAC TGTCACATTC TTTTAGGAA   120
CTGGGTTTGT AATTTCAGTT TCATCTGGGA AATGTGTAGC AGGAGGGCTT GAAGACAGTG  180
GTACACTGCC CTTAACATCA TCAGCTTCAA GGTCTGACAC                        220
```

Figure 1L

```
GTGTTGAGCC TGAATGGTAC ATTCCTATTA TTCCCATGGT GCTGATAAAT GGTGCTGAAG   60
GAATCGGTAC TGGGTGGTCC TGCAAAATCC CCAACTTTGA TGTGCGTGAA TTGTAAATA   120
ACATCAGGCG TTTGATGGAT GGAGAAGAAC CTTTGCCAAT GCTTCCAAGT              170
```

FIG. 9

```
CTTGATCCCT TCTGGTTGAT GCCAGAAGCT CTTCCTGATC CAGCATTTGT ATCTTCAATT   60
TCTCTACCAA TTGGCTTTGT TGGTTAATCT CTTCATCCTT GTCATCAAGT TGTTTATACA  120
ATTTAGCAAG TTCTTCTTCA CACTTTCTTC TTTCAGCATC GGTAAAACTA CCAGCCATTC  180
CGACTGCAGC AGCTGGTTTA TCACTGGTAA TAGCAATATC TTTATCCGCT GTGAAGGCTT  240
CCAAATTAGC TTTCTCTTTG TCAAACTGCT CATCAATAGG CACTGTCTCC CCGTTACGCC  300
AACGGTTTAG CTCGTTTTCC AGCCACT                                     327
```

FIG. 10

```
CCGACCGGGA GCGGGAGAAG GAGCGGGAGC GGGAGCAGCG GGAGAAGGAG CGGGAGAAGG   60
AGCTGGAGCG CGACGGGAGA AGGAACGGGA GCGCGAGCTG GAGCGGCAGC GGGAGCAGCG  120
GGCGAGGGAG AAGGAGCTGC TGGCTGCCAA GGCCTTAGAG CCCACCACCT TCCTGCCTGT  180
GGCCGAGCTG CACGGACTCC GAGGTCACAG CACGGAGGAG CGGCCCAAGC CCTCGGAGCA  240
GCTGACCCCA                                                         250
```

FIG. 11

```
CTCAGAGGTG ATCCTCTCGG AGTCGAGCTC AGGAGAAGGA GTCCCCTTCT TTGAGACTTG    60
GATGCAGACC TGCATGTCCG AGGAGGGCAA GATTTTGAAC CCTGACCATC CCTGCTTCCG   120
CCCTGACTCC ACCGAAGTCG AGTCCTTGGT GGCCCTGCTC AACAACTCTT CAGAGATGAA   180
GCTAGTACAG ATGAAGTAGC ACGAGGCC                                     208
```

FIG. 12A

```
CGACAAACAT CATCTGGGAA GACCCACACG ATGGAGGGTA AACTTCATGA TCCAGAAGGC    60
ATGGGAATTA TTCCAAGAAT AGTGCAAGAT ATTTTTAATT ATATTTACTC CATGGATGAA   120
AATTTGGAAT TTCATATTAA GGTTTCATAT TTTGAAATAT ATTTGGATAA GATAAGGGAC   180
TTGTTAGATG TTTCAAAGAC TAACCTTTCA GTCCATGAAG ACAAAAACCG TGTTCCCTAT   240
GTAAAGGGGT GCACAGAACG TTTCGTGTGT AGTCCAGATG AAGTCATGAA TACCATAGAT   300
GAAGGGAAAT CCAACAGAGA TGTCGCAGTT ACAAATATGA ATGAACATAG CTCTAGGAGC   360
CACAGCATAT TTCTTATTAA TGTAAAACAA GAGAATACAC AAACGGAACA GAAACTCAGT   420
GGAAAGCTTT ATCTGGTTGA TTTAGCTGGC AGTGAGAAGG TTAGTAAGAC TGGGGCTGAA   480
GGTGCTGTGC TGGATGAAGC TAAGAACATC AAGAAGTCAC TTTCTGCACT TGGAAATGTC   540
ATTTCTGCTT TGGCAGAGGG CAGTACCTAT GTTCCCTTATC GAGATAGTAA AATGACCAGA   600
ATTCTTCAAG ATTCATTAGG TGGCAACTGT AGGACCACTA TTGTCATATG CTGCTCTCCA   660
TCATCATACA ATGAGTCTGA GACAAAGTCA ACACTCCCTCT TTGGTCAAAG GGCCAAAACA   720
ATTAAGAACA CAGTCTGTGT CAATGTAGAG TTAACTGCAG AGCAGTGGAA AAAGAAGTAT   780
```

FIG. 12B

```
GAAAAAGAAA AGGAAAAAAA TAAGACTCTA CGGAACACTA TTCAGTGGCT GGAAAACGAG    840
CTAAACCGTT GGCGTAACGG GGAGACAGTG CCTATTGATG AGCAGTTTGA CAAAGAGAAA    900
GCTAATTTGG AAGCCTTCAC AGCGGATAAA GATACTGCTA TTACCAGTGA TAAACCAGCT    960
GCTGCAGTCG GAATGGCTGG TAGTTTTACC GATGCTGAAA GAAGAAAGTG TGAAGAAGAA   1020
CTTGCTAAAT TGTATAAACA GCTTGATGAC AAGGATGAAG AGATTAACCA ACAAAGCCAA   1080
TTGGTAGAGA AATTGAAGAC ACAAAATGCTG GATCAGGAAG AGCTTCTGGC ATCAACCAGA   1140
AGGGATCAAG ATAATATGCA AGCTGAACTG AATCGCCTCC AAGCAGAAAA TGATGCTTCT   1200
AAAGAAGAAG TCAAAGAAGT TTTACAGGCC TTAGAGGAAC TGGCTGTTAA TTATGATCAG   1260
AAGTCTCAGG AAGTTGAAGA CAAAACAAAG GAATATGAAT TGCTTAGTGA TGAATTGAAT   1320
CAAAAATCTG CAACTTTAGC AAGTATTGAT GCTGAGCTTC AGAAGCTGAA GGAAATGACC   1380
AACCACCAGA AGAAACGAGC AGCTGAAATG ATGGCATCAT TATTAAAAGA CCTTGCAGAA   1440
ATAGGAATTG CTGTGGGGAA TAACGATGTG AAGCAACCAG AAGGAACTGG TATGATAGAT   1500
GAAGAGTTTA CTGTTGCAAG ACTCTACATT AGCAAAAATGA AATCAGAAGT AAAGACCATG   1560
```

FIG. 12C

```
GTGAAACGCT GCAAACAGCT AGAAAGCACG CAGACTGAGA GCAACAAAAA AATGGAAGAA     1620
AATGAGAAAG AGTTAGCAGC ATGCCAGCTT CGGATCTCCC AACATGAAGC CAAAATCAAG     1680
TCACTGACTG AGTACCTTCA GAATGTAGAA CAAAGAAGA GGCAGCTGGA GGAATCTGTT      1740
GATTCCCTTG GTGAGGAGCT AGTCCAACTC CGAGCACAAG AGAAAGTCCA TGAAATGGAA     1800
AAAGAGCACT TGAACAAGGT TCAGACTGCA AATGAAGTCA AGCAAGCTGT TGAGCAGCAG     1860
ATCCAGAGTC ACAGAGAAAC CCACCAAAAA CAAATCAGTA GCTTGCGAGA TGAAGTTGAG     1920
GCAAAGGAAA AGCTAATCAC TGACCTCCAA GACCAAAACC AGAAGATGGT GTTGGAGCAG     1980
GAACGGCTAA GGGTGGAGCA TGAGAGGCTG AAGGCTACAG ACCAAGAGAA GAGCAGGAAG     2040
CTGCATGAGC TCACGGTTAT GCAAGACAGA CGAGAACAAG CAAGACAAGA CTTGAAGGGT     2100
TTGGAGGAGA CCGTGGCAAA AGAACTTCAG ACTTTACACA ACCTGCGTAA GCTCTTTGTT     2160
CAGGACTTGG CTACCAGGGT GAAAAAGAGG CCGAGGTCGA CTCTGACGAC ACTGGGGGCA     2200
GTGCTGCACA GAAGCAGAAA ATCTCCCTTCC TTGAAAACAA CCTTGAACAG CTCACCAAAG     2280
TGCACAAGCA GTTGGTACGT GATAATGCAG ATCTTCGCTG TGAGCTTCCT AAGTTAGAGA     2340
AACGGGCTTAG AGCTACTGCA GAAAGAGTGA AAGCTTTGGA GTCAGCCCG                2389
```

Act D
[µg/mL]

Camptothecin
[μg/mL]

Colchicine
[μg/mL]

Adriamycin
[μg/mL]

Etoposide
[μg/mL]

no infection     insert-free vector     anti-khcs GSE

GENES AND GENETIC ELEMENTS ASSOCIATED WITH SENSITIVITY TO CHEMOTHERAPEUTIC DRUGS

This application is a continuation of application Ser. No. 08/033,086, filed Mar. 9, 1993, which is a continuation-in-part of U.S. National Phase patent application, Ser. No. 08/039,385, filed Apr. 15, 1993, corresponding to International Patent Application No. PCT/US91/07492, filed 11 Oct. 1991 and published under International Publication No. WO 92/0701 on 30 Apr. 1992, which is a continuation-in-part of U.S. Ser. No. 07/599,730, filed Oct. 19, 1990, now U.S. Pat. No. 5,217,889, issued Jun. 8, 1993.

BACKGROUND OF THE INVENTION

1. Field of the Invention

The invention relates to genetic factors associated with sensitivity to chemotherapeutic drugs. More particularly, the invention relates to methods for identifying such factors as well as to uses for such factors.

2. Summary of the Related Art

A broad variety of chemotherapeutic agents are used in the treatment of human cancer. For example the textbook *CANCER: Principles & Practice Of Oncology*, 2d Edition, (De Vita et al., Eds.), J. B. Lippincott Company, Philadelphia, Pa. (1985) discloses as major antineoplastic agents the plant alkaloids vincristine, vinblastine, vindesine, and VM-26; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, cis-diamminedichloroplatinum, azetidinylbenzoquinone; and the miscellaneous agents dacarbazine, mAMSA and mitoxantrone.

These and other chemotherapeutic agents such as etoposide and amsacrine have proven to be very useful in the treatment of cancer. Unfortunately, some tumor cells become resistant to specific chemotherapeutic agents, in some instances even to multiple chemotherapeutic agents. Such drug resistance or multiple drug resistance can theoretically arise from either the presence of genetic factors that confer resistance to the drugs, or from the absence of genetic factors that confer sensitivity to the drugs. The former type of factors have been identified, and include the multiple drug resistance gene mdr-1 (see Chen et al., Cell 47:381–389 (1986)). However, the latter type of factor remains largely unknown, perhaps in part because such absence of factors would tend to be a recessive trait.

Identification of genes associated with sensitivity to chemotherapeutic agents is desirable, because the discovery of such genes can lead to both diagnostic and therapeutic approaches for cancer cells and for drug resistant cancer cells, as well as to improvements in gene therapy and rational drug design. Recently, some developments have been made in the difficult area of isolating recessive genetic elements, including one involved in cytotoxic drug sensitivity. Roninson et al., U.S. Pat. No. 5,217,889 (Ser. No. 07/599,730; allowed Sep. 9, 1992) teaches a generalized method for obtaining genetic suppressor elements (GSEs), which are dominant negative factors that confer the recessive-type phenotype for the gene to which the particular GSE corresponds. (See also Holzmayer et al., Nucleic Acids Res. 20:711–717 (1992)). Gudkov et al., Proc. Natl. Acad. Sci. USA (1993) [in press as of filing date] teaches isolation of GSEs inducing resistance to topoisomerase II-interactive drugs from topoisomerase II cDNA. However, there remains a need for identifying yet unknown genes or genetic elements associated with sensitivity to chemotherapeutic agents, a task made more difficult by the unavailability of a cloned gene as starting material for preparing GSEs. Preferably, such genes or genetic elements will be involved in a common pathway that is implicated in sensitivity to more than one chemotherapeutic agent. Most preferably, such genes or genetic elements will be identified by direct selection of GSEs causing loss of the drug sensitivity phenotype.

BRIEF SUMMARY OF THE INVENTION

The invention provides genetic suppressor elements (GSEs) that confer upon cells resistance to chemotherapeutic drugs. These GSEs are random fragments derived from genes associated with sensitivity to chemotherapeutic drugs, although the nature of such genes can be quite surprising.

In a first aspect, the invention provides a method for identifying GSEs that confer resistance to any chemotherapeutic drug for which resistance is possible. This method utilizes chemotherapeutic drug selection of cells that harbor clones from a random fragment expression library derived from total cDNA and subsequent rescue of library inserts from drug-resistant cells. In a second aspect, the invention provides a method for identifying and cloning genes that are associated with sensitivity to chemotherapeutic drugs, including genes that have not been previously discovered. This method comprises the steps of screening a full length cDNA library with a GSE that confers upon cells resistance to chemotherapeutic (or an oligonucleotide or polynucleotide constituting a portion of such a GSE) and determining the nucleotide sequence of the cDNA insert of any positive clones obtained. In a third aspect, the invention provides a method for obtaining GSEs having optimized suppressor activity for a gene associated with sensitivity to a chemotherapeutic drug. This method utilizes chemotherapeutic drug selection of cells that harbor clones from a random fragment expression library derived from DNA of a gene associated with sensitivity to the same chemotherapeutic drug, and subsequent rescue of the library inserts from drug resistant cells. In a fourth aspect, the invention provides synthetic peptides and oligonucleotides that confer upon cells resistance to chemotherapeutic drugs. These synthetic peptides and oligonucleotides are designed based upon the sequence of a drug-resistance conferring GSEs according to the invention.

In a fifth aspect, the invention provides a diagnostic assay for tumor cells that are resistant to one or more chemotherapeutic drug due to the absence of expression or underexpression of a particular gene. This diagnostic assay comprises quantitating the level of expression of the particular gene product by a particular tumor cell sample to be tested. In a sixth aspect, the invention provides dominant selectable markers that are useful in gene co-transfer studies. These dominant selectable markers are drug resistance-conferring GSEs according to the invention operably linked to appropriate transcriptional control elements. In a seventh aspect, the invention provides in vivo-selectable markers that are useful both for gene therapy and for enhanced chemotherapy for cancer. Such in vivo selectable markers are transferred into blood progenitor cells, which are then used to repopulate the patient's blood exclusively with cells that contain a co-transferred therapeutic gene, or for chemotherapy, just the chemotherapeutic drug resistance conferring GSE. In an eighth aspect, the invention provides a starting point for the rational design of pharmaceutical products that are useful against tumor cells that are resistant to chemotherapeutic drugs. By examining the structure, function, localization and pattern of expression of genes associated with sensitivity to chemotherapeutic drugs, strategies can be developed for creating pharmaceutical products that will overcome drug resistance in tumor cells in which such genes are either not expressed or underexpressed.

BRIEF DESCRIPTION OF THE DRAWINGS

FIG. 1 shows the nucleotide sequences of twelve GSEs that confer etoposide resistance upon cells and that were derived from topoisomerase II DNA, using a single gene random fragment expression library, as described in Example 1. The GSEs shown are (A) clone 2 V [SEQ. ID. NO. 1], (B) clone Σ11 [SEQ. ID. NO. 2], (C) clone 6 [SEQ. ID. NO. 3], (D) clone 5 [SEQ. ID. NO. 4], (E) clone Σ28 [SEQ. ID. NO. 5], (F) clone Σ2 [SEQ. ID. NO. 6], (G) clone Σ20 [SEQ. ID. NO. 7], (H) clone 39 [SEQ. ID. NO. 8], (I) clone 12S [SEQ. ID. NO. 9], (J) clone Σ8 [SEQ. ID. NO. 10], (K) clone ΣVPs2 [SEQ. ID. NO. 11], and (L) clone ΣVM [SEQ. ID. NO. 12].

FIG. 9 shows the nucleotide sequence of the GSE anti-khcs [SEQ. ID. NO. 15].

FIG. 10 shows the nucleotide sequence of the GSE VPA [SEQ. ID. NO. 16].

FIG. 11 shows the nucleotide sequence of the GSE VP9-11 [SEQ. ID. NO. 17].

FIG. 12 shows the nucleotide sequence of the most of the coding region of the mouse khcs cDNA [SEQ. ID. NO. 18].

DETAILED DESCRIPTION OF THE PREFERRED EMBODIMENTS

Figure 2A:
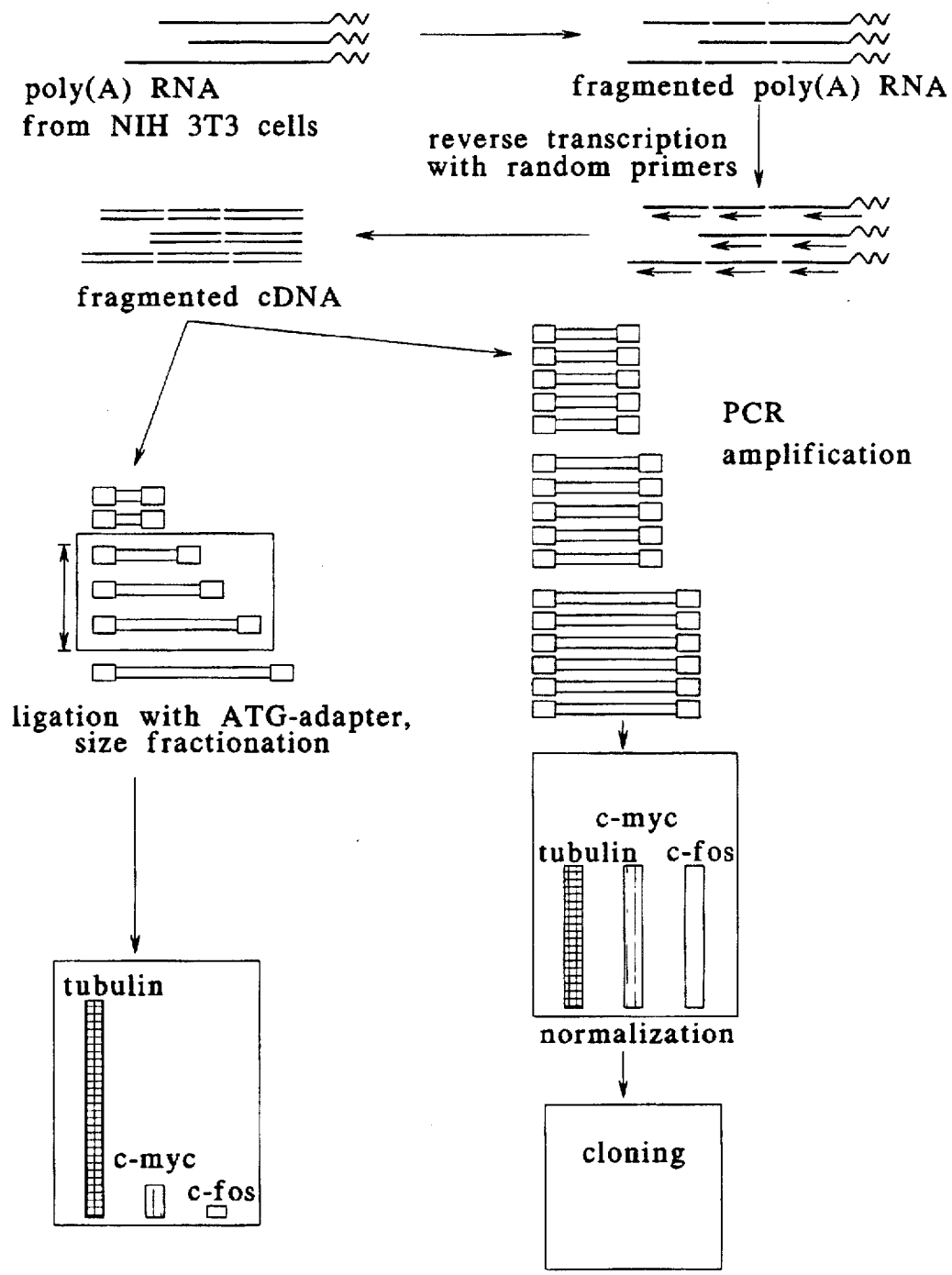
FIG. 2 shows a scheme for construction of RFEL from NIH 3T3 cDNA. Panel A shows the overall construction scheme. Panel B shows normalization of the cDNA fragments. In this panel, t represents total unfractionated cDNA, s and d represent the single-stranded and double-stranded fractions separated by hydroxyapatite, time points indicate the period of reannealing, and tubulin, c-myc, and c-fos indicate the probes used in Southern hybridization with the total, single-stranded and double-stranded fractions.

The invention relates to means for suppressing specific gene functions that are associated with sensitivity to chemotherapeutic drugs. The invention provides genetic suppressor elements (GSEs) that have such suppressive effect and thus confer resistance to chemotherapeutic drugs. The invention further provides methods for identifying such GSEs, as well as methods for their use.

In a first aspect, the invention provides a method for identifying GSEs that confer resistance to any chemotherapeutic drug for which resistance is possible. The GSEs identified by this method will be homologous to a gene that is associated with sensitivity to one or more chemotherapeutic drug. For purposes of the invention, the term "homologous to a gene" has two different meanings, depending on whether the GSE acts through an antisense or antigene mechanism, or rather through a mechanism of interference at the protein level. In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene.

The method according to this aspect of the invention comprises the step of screening a total cDNA or genomic DNA random fragment expression library phenotypically to identify clones that confer resistance to a chemotherapeutic drug. Preferably, the library of random fragments of total cDNA or genomic DNA is cloned into a retroviral expression vector. In this preferred embodiment, retrovirus particles containing the library are used to infect cells and the infected cells are tested for their ability to survive in a concentration of a chemotherapeutic drug that kills uninfected cells. Preferably, the inserts in the library will range in size from about 100 b.p. to about 700 b.p. and more preferably, from about 200 b.p. to about 500 b.p. Most preferably, the random fragment library will be a normalized library containing roughly equal numbers of clones corresponding to each gene expressed in the cell type from which it was made, without regard for the level of expression of any gene. However, normalization of the library is unnecessary for the isolation of GSEs that are homologous to abundantly or moderately expressed genes. Once a clonal population of cells that are resistant to the chemotherapeutic drug has been isolated, the library clone encoding the GSE is rescued from the cells. At this stage, the insert of the expression library may be tested for its nucleotide sequence. Alternatively, the rescued library clone may be further tested for its ability to confer resistance to chemotherapeutic drugs in additional transfection or infection and selection assays, prior to nucleotide sequence determination. Determination of the nucleotide sequence, of course, results in the identification of the GSE. This method is further illustrated in Examples 2–5.

In a second aspect, the invention provides a method for identifying and cloning genes that are associated with sensitivity to chemotherapeutic drugs, including genes that have not been previously discovered. This is because GSEs, or portions thereof, can be used as probes to screen full length cDNA or genomic libraries to identify their gene of origin. In some cases, genes that are associated with sensitivity to chemotherapeutic drugs will turn out to be quite surprising. For example, GSEs that abrogate etoposide sensitivity are of a particularly surprising nature. The target for etoposide is topoisomerase II, a DNA unwinding enzyme. GSEs prepared from random fragments of topoisomerase II DNA do confer resistance to etoposide. Accordingly, it would be expected that most GSEs conferring etoposide resistance would be derived from DNA encoding toposisomerase II. Surprisingly, this is not the case at all. Of three etoposide resistance-conferring GSEs obtained, two were derived from previously unidentified DNA sequences. A third such GSE was derived from the kinesin heavy chain gene. Prior to this discovery, there was no suspicion that kinesin was in any way implicated in etoposide sensitivity. These results suggest that the method according to this aspect of the invention will provide much new and surprising information about the genetic basis for resistance to chemotherapeutic drugs. In addition, a kinesin-derived GSE conferring resistance to etoposide caused cellular effects suggesting that kinesin may be involved in programmed cell death. If this is indeed the case, then the method according to this aspect of the invention also provides valuable information about the genetic basis for senescence and cell death. This may have important implications for studying genes involved in development, since GSEs used to identify genes associated with chemotherapeutic drug resistance or senescence can also be expressed as transgenes in embryos to determine the role of such genes in development. The method according to this aspect of the invention and its use for studying genes identified thereby and their cellular effects are further illustrated in Examples 6–8.

In a third aspect, the invention provides a method for obtaining GSEs having optimized suppressor activity for a gene associated with sensitivity to a chemotherapeutic drug. In the method according to this aspect of the invention, an initial GSE is obtained by the method according to the first aspect of the invention. Then, the gene from which the GSE is derived is identified and cloned by the method according to the second aspect of the invention. This gene is then randomly fragmented and cloned into an expression vector, preferably a retroviral vector, to obtain a random fragment expression library derived exclusively from the gene of interest. This library is then transferred to and expressed in mammalian cells, which are selected in the presence of the appropriate chemotherapeutic drug. As a practical matter, such a library will contain a much greater variety of GSEs derived from the gene of interest than will a random fragment library prepared from total cDNA. Consequently, the likelihood of obtaining optimized GSEs, as determined by maximized chemotherapeutic drug resistance, from the single gene random fragment library is much higher. A single gene random fragment library approach is shown in greater detail in Example 1.

In a fourth aspect, the invention provides synthetic peptides and oligonucleotides that are capable of inhibiting the function of genes associated with sensitivity to chemotherapeutic drugs. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE is discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSEs have one critical endpoint, from which a simple walking experiment will determine the minimum size of peptide or oligonucleotide necessary to inhibit gene function. For peptides, functional domains as small as 6–8 amino acids have been identified for imunoglobulin binding regions. Thus, peptides or peptide mimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. As used herein, the term oligonucleotide includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art. (See e.g., Uhlmann and Peyman, Chemical Reviews 90:543–584 (1990); Schneider and Banner, Tetrahedron Letters 31:335 (1990)). The term oligonucleotides also includes oligonucleotides having modified bases or modified ribose or deoxyribose sugars.

In a fifth aspect, the invention provides a diagnostic assay for tumor cells that are resistant to one or more chemotherapeutic drug due to absence of expression or underexpression of a particular gene. By using the methods according to the first and second aspects of the invention such a gene will be identified and cloned. To determine whether absence of expression or underexpression of such a gene is a naturally occurring, and thus medically significant basis for chemotherapeutic drug resistance, human tumor cells can be treated with cytotoxic quantities of an appropriate chemotherapeutic drug to select for spontaneous drug resistant mutants. These mutants can then be assessed for their level of expression of the particular gene of interest. Absence of expression or significantly reduced expression indicates a natural mechanism of chemotherapeutic drug resistance. Accordingly, such reduced or absent expression can be the basis for a diagnostic assay for tumor cell resistance to the chemotherapeutic drug or drugs of interest. A first embodiment of a diagnostic assay according to this aspect of the invention utilizes an oligonucleotide or oligonucleotides that is/are homologous to the sequence of the gene for which expression is to be measured. In this embodiment, RNA is extracted from a tumor sample, and RNA specific for the gene of interest is quantitated by standard filter hybridization procedures, an RNase protection assay, or by quantitative cDNA-PCR. (See Noonan et al., Proc. Natl. Acad. Sci. USA 87:7160–7164 (1990)). In a second embodiment of a diagnostic assay according to this aspect of the invention, antibodies are raised against a synthetic peptide having an amino acid sequence that is identical to a portion of the protein that is encoded by the gene of interest. These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested.

In a sixth aspect, the invention provides dominant selectable markers that are useful in gene co-transfer studies. Since GSEs according to the invention confer resistance to chemotherapeutic drugs, the presence of a vector that expresses the GSE can readily be selected by growth of a vector-transfected cell in a concentration of the appropriate cytotoxic drug that would by cytotoxic in the absence of the GSE. GSEs according to the invention are particularly well suited as dominant selectable markers because their small size allows them to be easily incorporated along with a gene to be cotranfered even into viral vectors having limited packaging capacity.

In a seventh aspect, the invention provides in vivo-selectable markers that are useful both in gene therapy and in enhancing the effectiveness of chemotherapy. For gene therapy, GSEs according to the invention can be co-transferred on a vector into human CD34$^+$ blood progenitor cells from a patient along with a therapeutic gene that, when expressed, will alleviate a genetic disorder. The cells can be selected in vitro for resistance to an appropriate chemotherapeutic drug, thereby assuring successful transfer of the GSE, and by implication, of the therapeutic gene as well. The progenitor cells containing the GSE and therapeutic gene can then be returned to the patient's circulation. Finally, the cells containing the GSE and therapeutic gene can be selected in vivo by administration of the appropriate chemotherapeutic drug (to which the GSE confers resistance) in a concentration that is cytotoxic to normal blood cells. In this way, those cells having the GSE and therapeutic gene will repopulate the patient's blood.

For enhancement of chemotherapy, a GSE according to the invention can be transferred alone or with another gene on an expression vector into CD34$^+$ blood progenitor cells taken from a cancer patient. In vitro selection of the progenitor cells harboring the GSE is then carried out, using the appropriate chemotherapeutic drug. The selected cells are then returned to the patient's circulation and allowed time to begin repopulating the blood. After an appropriate period, aggressive chemotherapy can be carried out, using much higher than ordinary concentrations of an appropriate chemotherapeutic drug (to which the GSE confers resistance), since toxic side effects to the immune system will be avoided due to GSE expression in those cells.

In either of these therapeutic contexts, it may be desirable to have the GSE expressed in the progenitor cells (and subsequently in the blood cells), only when its expression is beneficial, i.e., during in vitro selection of cells harboring the GSE and again during in vivo selection or chemotherapy. To accomplish this, an inducible promoter can be used to express the GSE. Then, the appropriate inducing agent is added to the cells prior to and during in vitro selection and again prior to and during in vivo selection or chemotherapy. As long as the inducing agent is not normally present in the human body, the GSE will not be expressed at any other time.

In an eighth aspect, the invention provides a starting point for the rational design of pharmaceutical products that can counteract resistance by tumor cells to chemotherapeutic drugs. The protein sequence encoded by genes from which the GSEs were derived can be deduced from the cDNA sequence, and the function of the corresponding proteins may be determined by searching for homology with known genes or by searching for known functional motives in the protein sequence. If these assays do not indicate the protein function, it can be deduced through the phenotypic effects of the GSEs suppressing the gene. Such effects can be investigated at the cellular level, by analyzing various growth-related, morphological, biochemical or antigenic changes associated with GSE expression. The GSE effects at the organism level can also be studied by introducing the corresponding GSEs as transgenes in transgenic animals (e.g. mice) and analyzing developmental abnormalities associated with GSE expression. The gene function can also be studied by expressing the full-length cDNA of the corresponding gene, rather than a GSE, from a strong promoter in cells or transgenic animals, and studying the changes associated with overexpression of the gene.

Full-length or partial cDNA sequences can also be used to direct protein synthesis in a convenient prokaryotic or eukaryotic expression system, and the produced proteins can be used as immunogens to obtain polyclonal or monoclonal antibodies. These antibodies can be used to investigate the protein localization and as specific inhibitors of the protein function, as well as for diagnostic purposes. In particular, antibodies raised against a synthetic peptide encoded by part of the complement of the sequence of the GSE anti-khcs, or the corresponding region of the human KHCS protein should be particularly useful, as should antibodies raised against an amino acid sequence encoded by part of the VPA or VP9-11 GSEs (see FIGS. 9–11).

Understanding the biochemical function of a gene involved in drug sensitivity is likely to suggest pharmaceutical means to stimulate or mimic the function of such a gene and thus augment the cytotoxic response to anticancer drugs. For example, if the gene encodes an enzyme producing a certain compound, such a compound can be synthesized chemically and administered in combination with cytotoxic drugs. If a pharmaceutical approach is not apparent from the protein function, one may be able to upmodulate gene expression at the level of transcription. This can be done by cloning the promoter region of the corresponding gene and analyzing the promoter sequence for the presence of cis elements known to provide the response to specific biological stimulators.

The most straightforward way to increase the expression of a drug sensitivity gene, identified through the GSE approach, would be to insert a full-length cDNA for such a gene into a retroviral vector. Such a vector, in the form of a recombinant retrovirus, will be delivered to tumor cells in vivo, and, upon integration, would sensitize such cells to the effects of the corresponding chemotherapeutic drug. A similar strategy for selective delivery of a drug-sensitivity gene into rat brain tumors, followed by curative treatment with the appropriate drug, was reported by Culver et al., Science 256:1550–1552 (1992). The selective delivery to tumor cells can be accomplished on the basis of the selectivity of retrovirus-mediated transduction for dividing cells. Altenatively, the selectivity can be achieved by driving the expression of the drug sensitivity gene from a tissue- or tumor-specific promoter, such as, for example, the promoter of the carcinoembryonic antigen gene.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screening systems for new compounds with anticancer activity. Accordingly, mammalian cells that express chemotherapeutic drug resistance-conferring GSEs according to the invention are useful for screening compounds for the ability to overcome drug resistance.

The following examples are intended to further illustrate certain preferred embodiments of the invention and are not limiting in nature.

EXAMPLE 1

Development Of GSEs For Human Topoisomerase II

Topoisomerase II is a DNA unwinding enzyme that serves as a target for many anti-cancer drugs, including etoposide, doxorubicin and amsacrine. The enzyme normally acts by double-strand DNA cleavage, followed by strand passage and religation of the breaks. Anti-cancer drugs cause trapping of the enzyme in complexes having double-strand breaks held together by the enzyme, thereby leading to lethal damage in replicating cells. Some cell lines that are resistant to anti-cancer drugs that interact with topoisomerase II have decreased expression of this enzyme.

Random fragment selection of GSEs requires transfer of the expression library into a very large number of recipient cells. Therefore, to prepare a random fragment library containing GSEs for topoisomerase II, the efficient retroviral vector system was chosen. Overlapping cDNA clones spanning the entire coding sequence for topoisomerase II were mixed and randomly fragmented into 250–350 bp fragments by DNase I in the presence of $Mn^{++}$ ions and fragment termini were filled in with T4 DNA polymerase and Klenow fragment of DNA polymerase I. After ligation with a synthetic adaptor providing translation initiation and termination codons, the fragment mixture was amplified by PCR, using adaptor-derived primers. The amplified mixture was cloned into the LNCX retroviral vector which contains a neo gene. (see Miller and Rosman, Biotechniqes 7:980–986 (1989)).

A random fragment library containing 20,000 independent clones was obtained, and was used to transfect amphotropic and ecotropic virus-packaging cell lines derived from NIH 3T3 cells, to effect ping-pong replication-mediated amplification of the virus (e.g., see Bodine, et al. Proc. Natl. Acad. Sci. USA 87:3738–3742 (1990)). This resulted in a random fragment expression library (RFEL), a set of recombinant retroviruses containing a representative mixture of inserts derived from topoisomerase II gene sequences.

The uniformity of sequence representation in RFEL was monitored as follows. NIH 3T3 cells were infected with virus-containing supernatant, followed 24 hours later by PCR amplification of integrated proviral insert sequences in the presence of [$^{32}P$] alpha-dNTP. An aliquot of the PCR-amplified mixture was subjected to gel electrophoresis to establish the absence of predominant bands. Another aliquot was used as a probe for a Southern blot of topoisomerase II cDNA digested with several frequently cutting restriction enzymes. A representative sequence mixture was obtained, as evidenced by the absence of a predominant band in the first test, and uniform hybridization to all fragments in the second test.

RFEL was then used to infect HeLa cells, and the infectants were selected with G418. Colonies of G418-resistant cells, having about 50–70 cells each, were then exposed to etoposide at a concentration of 200 µg/ml. Approximately 50 of 10,000 G418-resistant colonies were etoposide resistant, compared to a frequency of <$10^{-4}$ when insertless retroviruses were used as a control. Cell lines were isolated from etoposide-resistant colonies. Amphotropic and ecotropic packaging cell lines producing RFEL were also selected for etoposide resistance. Virus from etoposide resistant packaging cell lines was used to infect HeLa cells, which were then selected with G418. G418-resistant infectants were challenged with three topoisomerase II-interactive anticancer drugs: etoposide, teniposide and amsacrine. A high proportion of infected cells were resistant to all three drugs, thus demonstrating that etoposide selection of mouse packaging cell lines has led to the generation of GSEs active in both human and mouse cells. These infectants were also used to establish cell lines. RFEL-derived inserts were recovered from etoposide resistant cell lines by PCR and recloned into LNCX vector. The newly-derived clones were then individually tested for the ability to confer resistance to etoposide upon transfection into HeLa cells, to confirm the GSE activity of the corresponding inserts.

Sequence analysis of 26 different isolated clones revealed that 16 of them were inserted in antisense and 10 in sense orientation. Of the 12 GSEs confirmed, 7 were sense and 5 antisense, as shown in Table I. The sequences of the confirmed GSEs are shown in FIG. 1. The sense-oriented inserts of the confirmed GSEs encode 37–99 amino acid long topo II-derived peptides, initiating either from the ATG codon provided by the adaptor, or from an internal ATG codon within the open reading frame of Topoisomerase II, located close to the 5' end of the insert in an appropriate context for translation initiation. Four of the confirmed antisense GSEs come from the 3' third of the cDNA and one from the 5' end of cDNA, including the translation start site. Of the sense-oriented GSEs, five are derived from the central portion of the protein that includes the active site tyrosine-804 that covalently binds to DNA and the "leucine zipper" region involved in dimerization of Topoisomerase II. One GSE peptide is derived from the region near the N-terminus and another from the region near the C-terminus of the protein; no known functional sites are associated with either segment.

TABLE I

Confirmed Topoisomerase II-Derived GSE

| Clones | Orientation (Sense/Antisense) | Position in cDNA[a] | Position of peptide[b] |
|---|---|---|---|
| 2V | Antisense | −18–145 | |
| Σ11 | Sense | 393–605 | 134–201 |
| 6 | Sense | 2352–2532 | 808–844 |
| 5 | Sense | 2511–2734 | 846–911 |
| Σ28 | Sense | 2603–2931 | 879–977 |
| Σ2 | Antisense | 3150–3343 | |
| Σ20 | Antisense | 3486–3692 | |
| 39 | Antisense | 3935–4127 | |
| 12S | Sense | 4102–4343 | 1368–1447 |
| ΣVPs2 | Sense | 2494–2834 | 846–944 |
| Σ8 | Antisense | 4123–4342 | |
| ΣVM | Sense | 2501–2670 | 846–890 |

[a]Position in the cDNA sequence of topoisomerase II; residues numbered as in Tsai-Pflugfelder et al., Proc. Natl. Acad. Sci. USA 85:7177–7181 (1988).
[b]Position of the peptide encoded by sense-oriented GSEs in the amino acid sequence of topoisomerase II; translation assumed to initiate from the first ATG codon in the correct open reading frame.

These results demonstrate that GSEs that act according to multiple mechanisms to confer etoposide resistance can be prepared from a random fragment library of DNA encoding topoisomerase II. In addition, these results show that GSEs produced from one mammalian species can be active in another mammalian species.

EXAMPLE 2

Figure 2B:
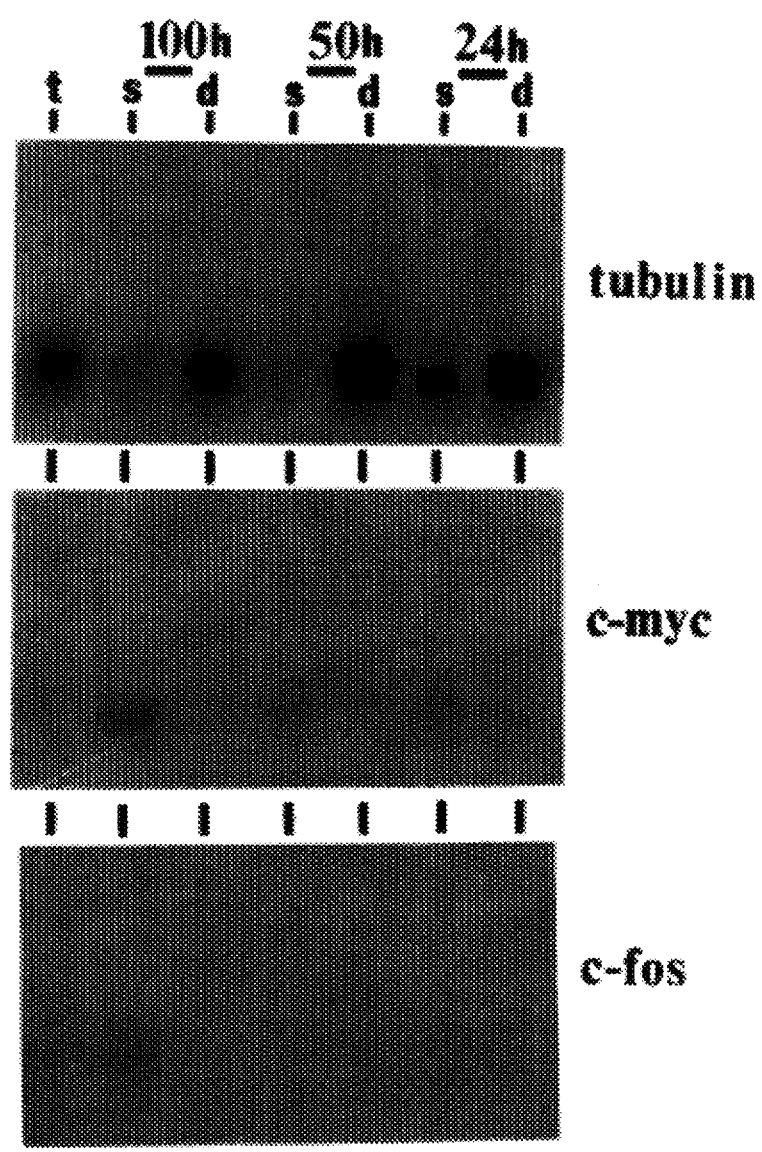
Figure 3A:
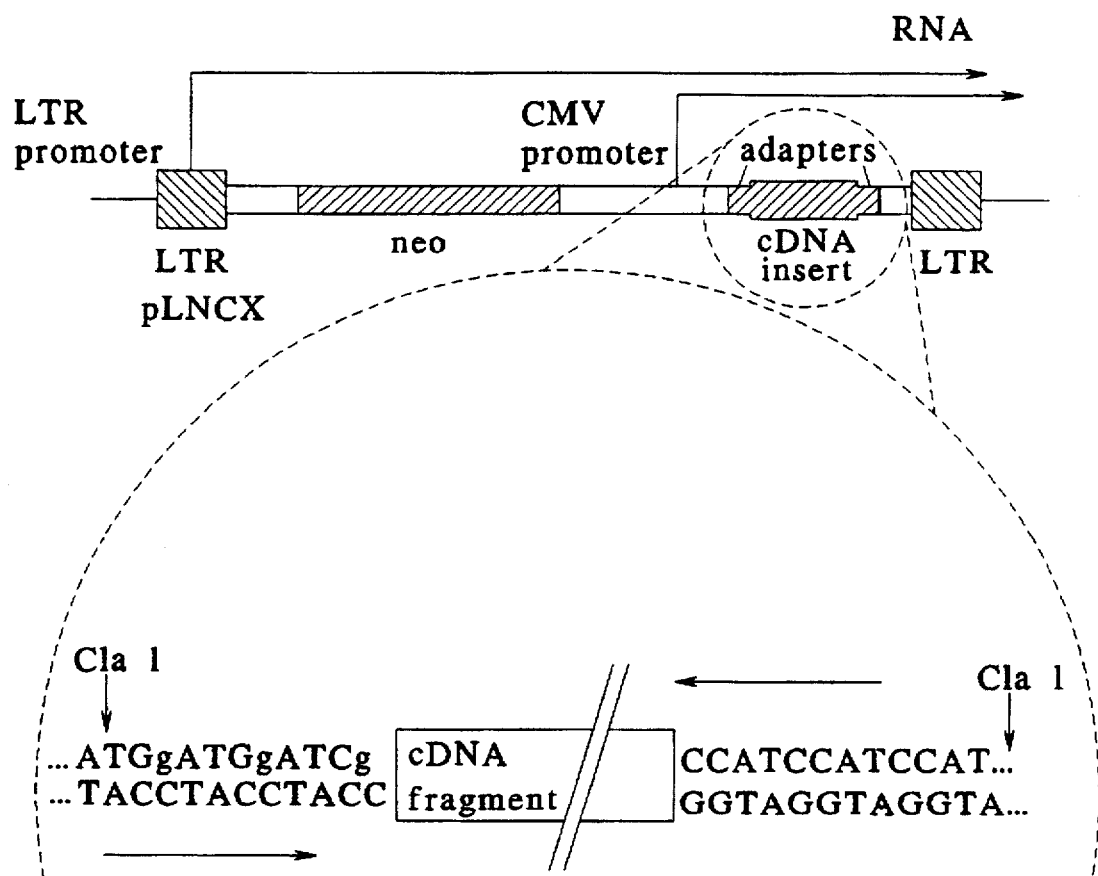
FIG. 3 shows the structure of the LNCX vector and the adaptor used for cDNA cloning. The nucleotide sequences are shown for the ATG-sense [SEQ. ID. NO. 13] and ATG-antisense [SEQ. ID. NO. 14] strands of the adaptor.
Figure 3B:
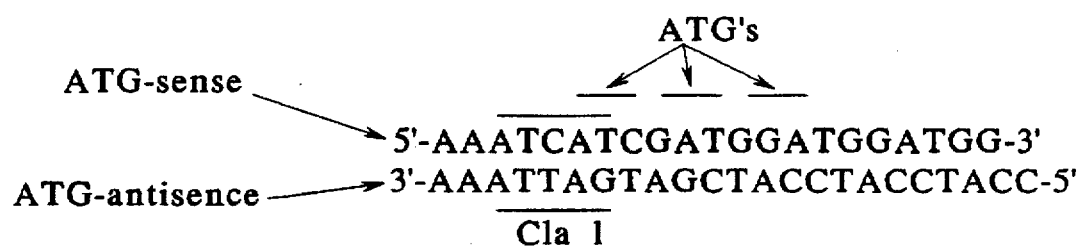

Generation Of A Normalized Random Fragment cDNA Library In A Retroviral Vector As shown in FIG. 2 a normalized cDNA population was prepared using a modification of the protocol of Patanjali et al., Proc. Natl. Acad. Sci. USA 88:1943–1947 (1991). Poly (A)$^+$ RNA was extracted from NIH 3T3 cells. To obtain mRNAs for different genes expressed at various stages of the cell growth, one half of the RNA was isolated from a rapidly growing culture and the other half from quiescent cells that had reached complete monolayer confluency. To avoid over-representation of the 5'-end sequences in a randomly primed cDNA population, RNA was fragmented by boiling to an average size range 600–1,000 nucleotides. These RNA fragments were then used for preparing randomly primed double-stranded cDNA. This randomly primed cDNA was then ligated to a synthetic adaptor providing ATG codons in all three possible reading frames and in a proper context for translation initiation. The structure of the adaptor (see FIG. 3) determined its ligation to the blunt-ended fragments of the cDNA in such a way that each fragment started from initiation codons independently from its orientation. The adaptor was not supplied with termination codons in the opposite strand since the cloning vector pLNCX, contained such codons immediately downstream of the cloning site. This vector has been described by Miller and Rosman, Biotechniques 7:980–986 (1989). The ligated mixture was amplified by PCR, using the "sense" strand of the adaptor as a PCR primer, in contrast to the method of Patanjali et al., which utilized cloning the initial cDNA preparation into a phage vector and then using vector-derived sequences as PCR primers to amplify the cDNA population. The PCRs were carried out in 12 separate reactions that were subsequently combined, to minimize random over- or under-amplification of specific sequences and to increase the yield of the product. The PCR-amplified mixture was size-fractionated by gel electrophoresis, and 200–500 bp fragments were selected for subsequent manipulations in contrast to Patanjali's fragment size range of from 400 to 1,600 bp.

For normalization, the cDNA preparation was denatured and reannealed, using different time points, as described by Patanjali et al., supra, and shown in FIG. 2, for reannealing. The single-stranded and double-stranded DNAs from each reannealed mixture were separated by hydroxyapatite chromatography. The single-stranded DNA fractions from each time point of reannealing were PCR-amplified using the adaptor-derived primer and analyzed by Southern hybridization for the relative abundance of different mRNA sequences. The fraction that contained similar proportions of tubulin, c-myc and c-fos cDNA sequences (see FIG. 2), corresponding to high-, medium- and low-expressed genes, respectively, was used for the library preparation.

The normalized cDNA preparation was cloned into the Cla I site of the MoMLV-based retroviral vector pLNCX, which carries the neo (G418 resistance) gene, transcribed from the promoter contained in the retroviral long terminal repeat (LTR), and which expresses the inserted sequence from a strong promoter of the cytomegalovirus (CMV) (see FIG. 3). The ligation mixture, divided into five portions, was used for five subsequent large-scale transformations of E.coli. The transformed bacteria were plated on the total of 500 agar plates (150 mm in diameter) and the plasmid population (18 mg total) was isolated from the colonies washed off the agar. A total of approximately $5 \times 10^7$ clones were obtained, more than 60% of which carried the inserts of normalized cDNA, as estimated by PCR amplification of inserts from 50 randomly picked colonies. These results demonstrate the feasibility of generating a normalized cDNA library of as many as $3 \times 10^7$ recombinant clones in a retroviral plasmid expression vector.

EXAMPLE 3

Transduction Of A Retroviral Random Fragment Library Into Virus-Packaging Cell Lines And NIH 3T3 Cells The plasmid library prepared according to Example 2 was converted into a mixture of retroviral particles by transfection into virus-packaging cells (derivatives of NIH 3T3) that express retroviral virion proteins. Examples of such cell lines have been described by Markowitz et al., Virology 167:400–406 (1988). Ecotropic and amphotropic virus-packaging cell lines, GP+E86 and GP+envAm12, respectively, were mixed at a 1:1 ratio, and $10^7$ cells of this mixture were transfected with the plasmid library under standard calcium phosphate coprecipitation conditions. This transfection resulted in the packaging and secretion of ecotropic and amphotropic virus particles, which rapidly spread through the packaging cell population, since ecotropic viruses are capable of infecting amphotropic packaging cells and vice versa. The yield of the virus, as measured by the number of G418-resistant colonies obtained after the infection of NIH 3T3 cells, reached $10^5$ infectious units per 1 ml of media during the stage of transient transfection (1–3 days), then decreased (4–8 days) and then rapidly increased due to the expression of proviral genomes that became stably integrated in most of the packaging cells. The yield of the virus 9–12 days after transfection reached >$10^6$ per 1 ml of media supernatant. At this stage, the library showed fairly even representation of different fragments, but at later stages individual virus-producing clones began to predominate in the population, leading to uneven representation of cDNA-derived inserts. The uniformity of sequence representation in the retroviral population was monitored by rapid extraction of DNA from cells infected with the virus-containing supernatant, followed by PCR amplification of inserts. The inserts were analyzed first by the production of a continuous smear in ethidium-bromide stained agarose gel and then by Southern hybridization with different probes, including topiosomerase II, c-myc and tubulin. As long as each gene was represented by a smear of multiple fragments, the representativity of the library was considered to be satisfactory.

In other experiments, for transducing the random-fragment normalized cDNA library into NIH 3T3 cells, without loss of representativity, NIH 3T3 cells were infected either with a virus produced at the transient stage of transfection (days 1–3), or with the high-titer virus collected 10–12 days after transfection. In the latter case, 100 ml of vital suspension contained more than $10^8$ infectious units. In the case of the "transient" virus, NIH 3T3 cells were infected with at least $10^7$ recombinant retroviruses by using 500 ml of media from virus-producing cells (five rounds of infection, 100 ml of media in each). These results demonstrate the feasibility of converting a large and complex random fragment library into retroviral form and delivering it to a non-packaging cell line without loss of complexity.

EXAMPLE 4

Isolation Of GSEs Conferring Resistance To The Chemotherapeutic Drug Etoposide

Figure 4:
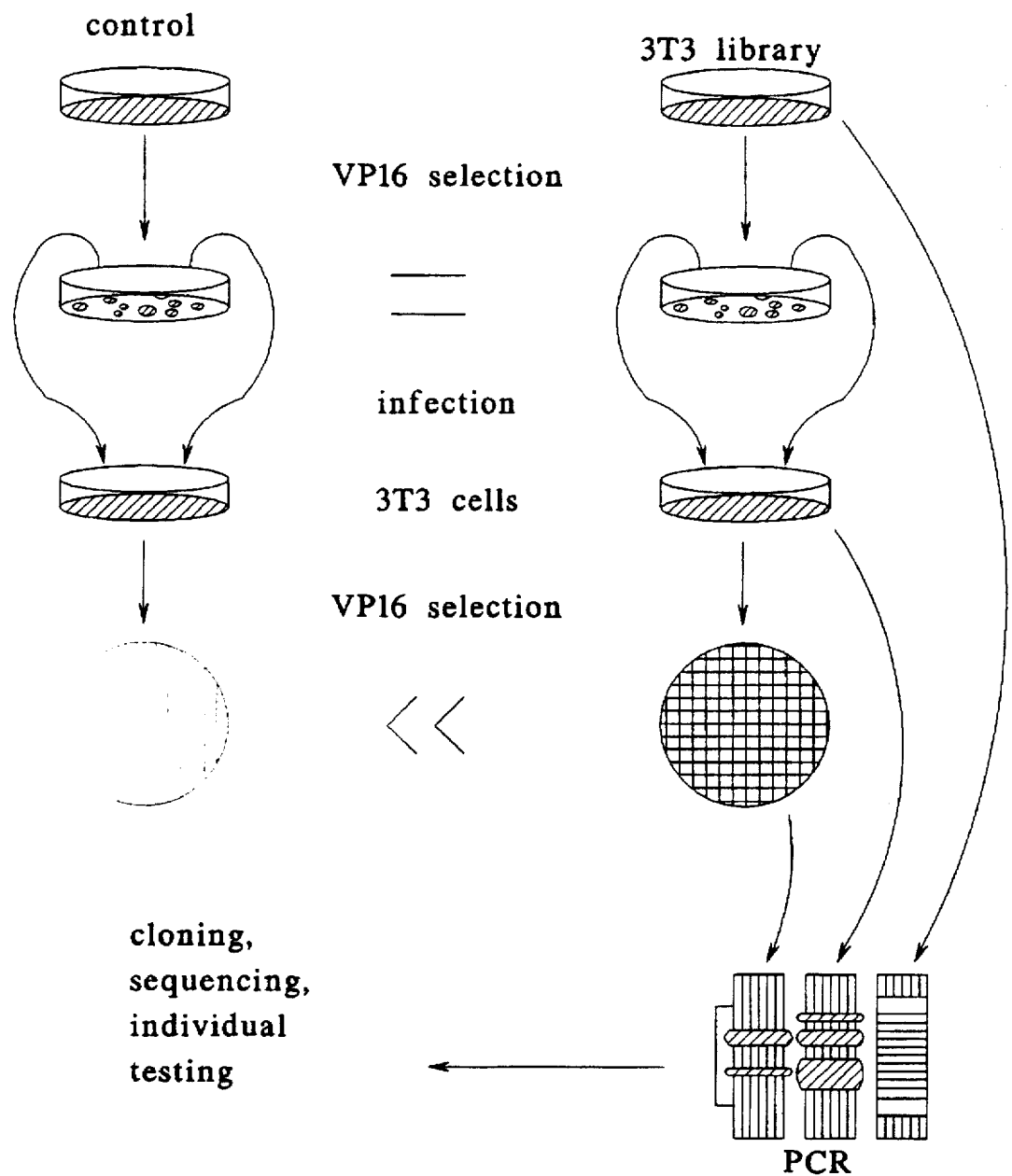
FIG. 4 shows the overall scheme for selecting cell lines containing chemotherapeutic drug resistance-conferring GSEs and rescuing the GSEs from these cells.
Figure 5A:
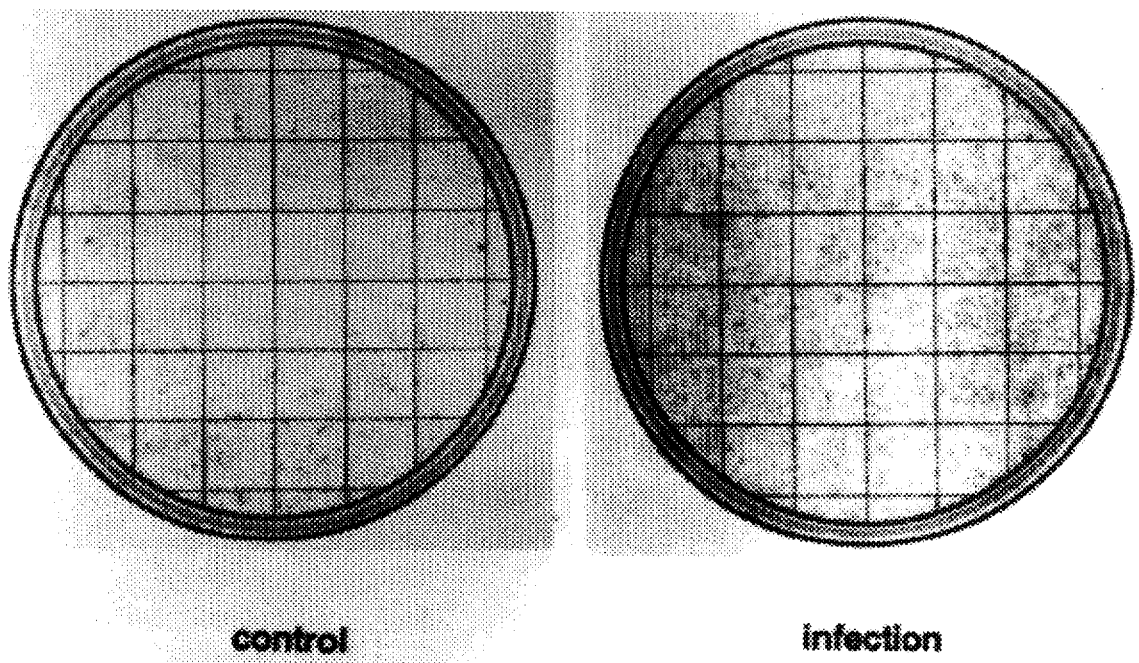
FIG. 5 shows etoposide resistance conferred by preselected virus (Panel A) and PCR analysis of the selected and unselected populations (Panel B).

The overall scheme for the selection of GSEs conferring etoposide resistance is illustrated in FIG. 4. This selection was carried out directly on virus-producing packaging cells, in the expectation that cells whose resistant phenotype is caused by the GSE expression will produce virus particles carrying such a GSE. The mixture of amphotropic and ecotropic packaging cells was transfected with the cDNA library in the LNCX vector, prepared according to Example 2 and the virus was allowed to spread through the population for 9 days. Analysis of a small part of the population for G418 resistance showed that practically 100% of the cells carried the neo-containing provirus. The cells were then exposed to 350 ng/ml etoposide for 15 days and then allowed to grow without drug for two more weeks. No difference was observed between the numbers of colonies obtained in the experiment and in the control (uninfected cells or cells infected with the insert-free LNCX virus) after etoposide selection. The virus present in the media supernatant of the surviving cells was then used to infect NIH 3T3 cells followed by etoposide selection using essentially the same protocol. NIH 3T3 cells infected with the library-derived virus produced by packaging cells that were selected with etoposide showed a major increase in the number of etoposide-resistant cells relative to the control cells infected with the insert-free LNCX virus, indicating the presence of biologically active GSEs in the preselected virus population (see FIG. 5A).

Figure 5B:
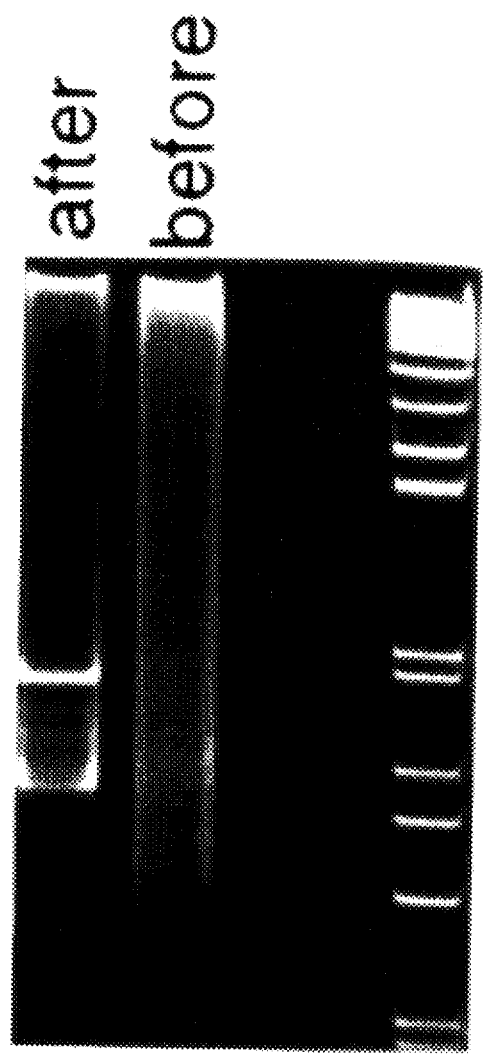
Figure 6:
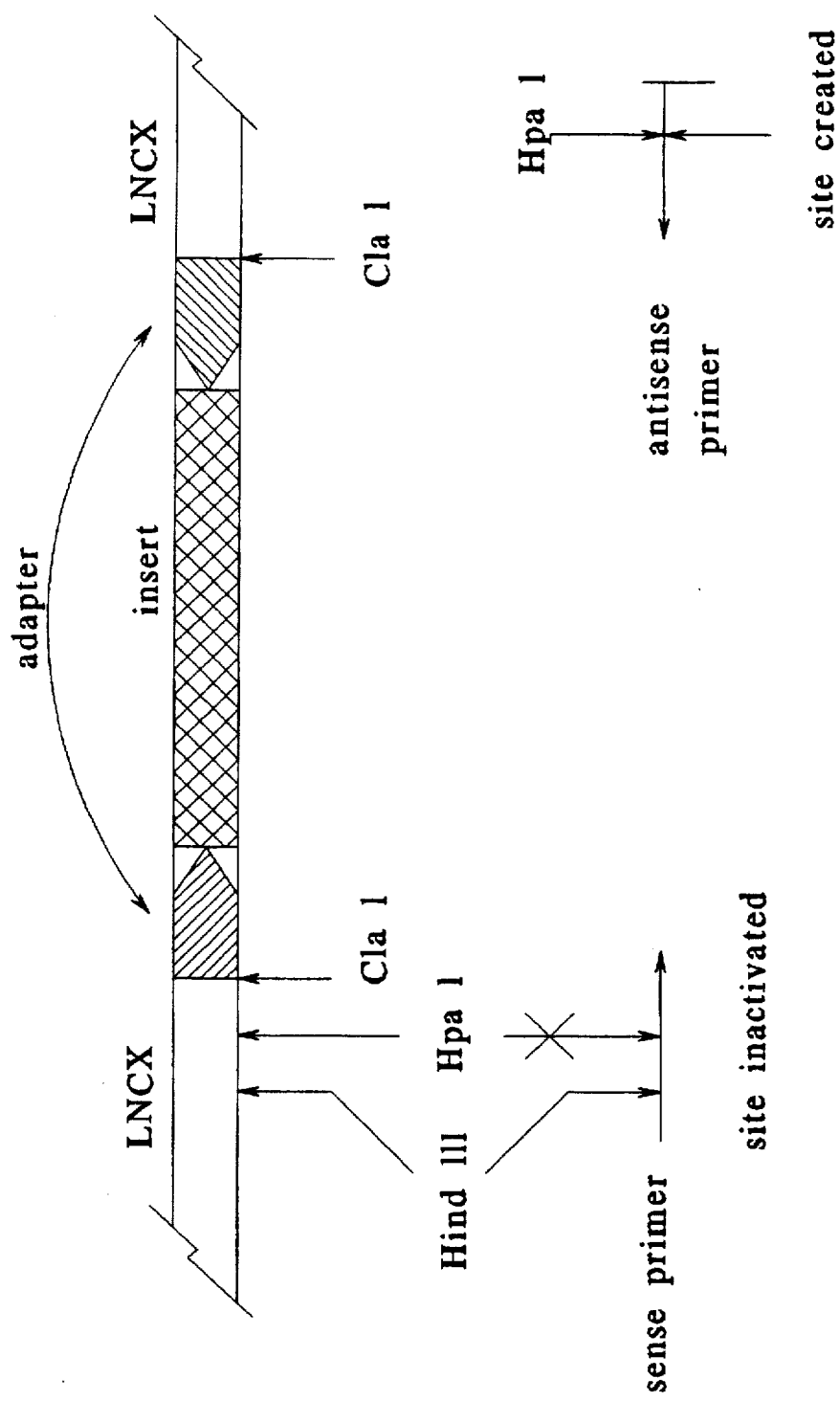
FIG. 6 shows a scheme for recloning individual PCR-amplified fragments from etoposide resistant selected cells into the LNCX vector, as described in Example 4.
Figure 7A:
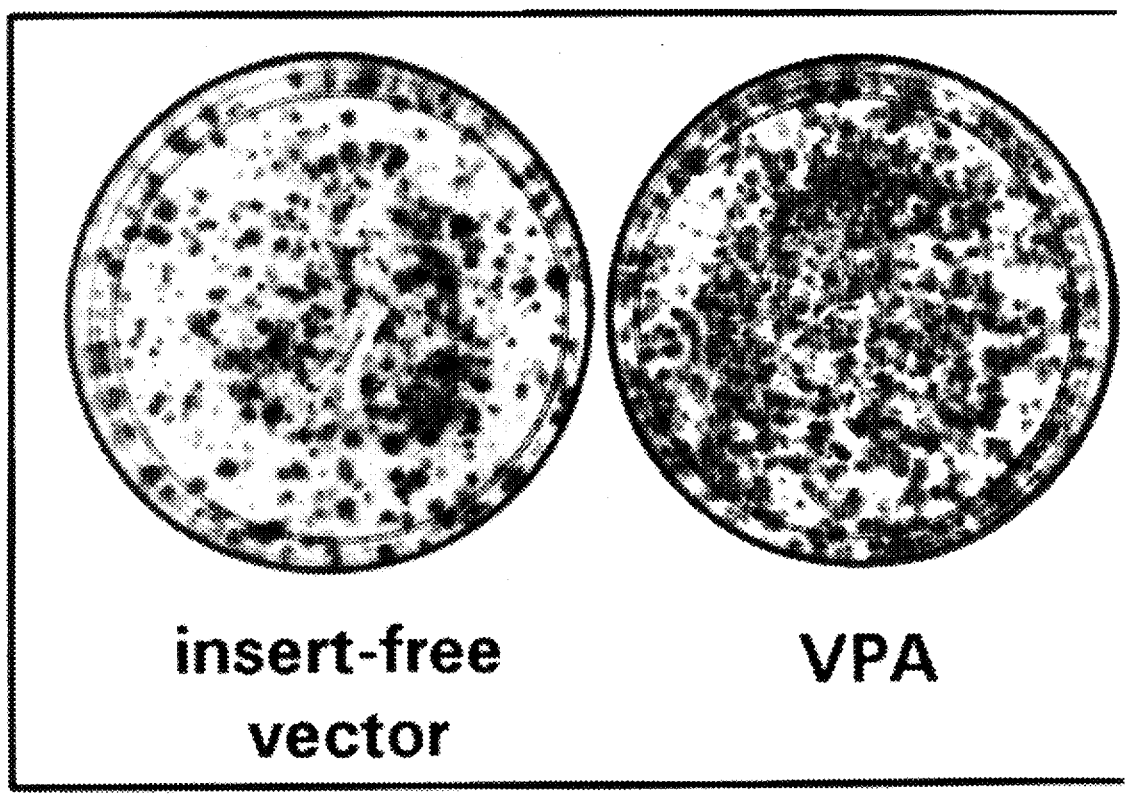
FIG. 7 demonstrates resistance to 350 ng/ml etoposide, conferred upon the cells by the GSEs VPA (Panel A) and VP9-11 (Panel B).
Figure 7B:
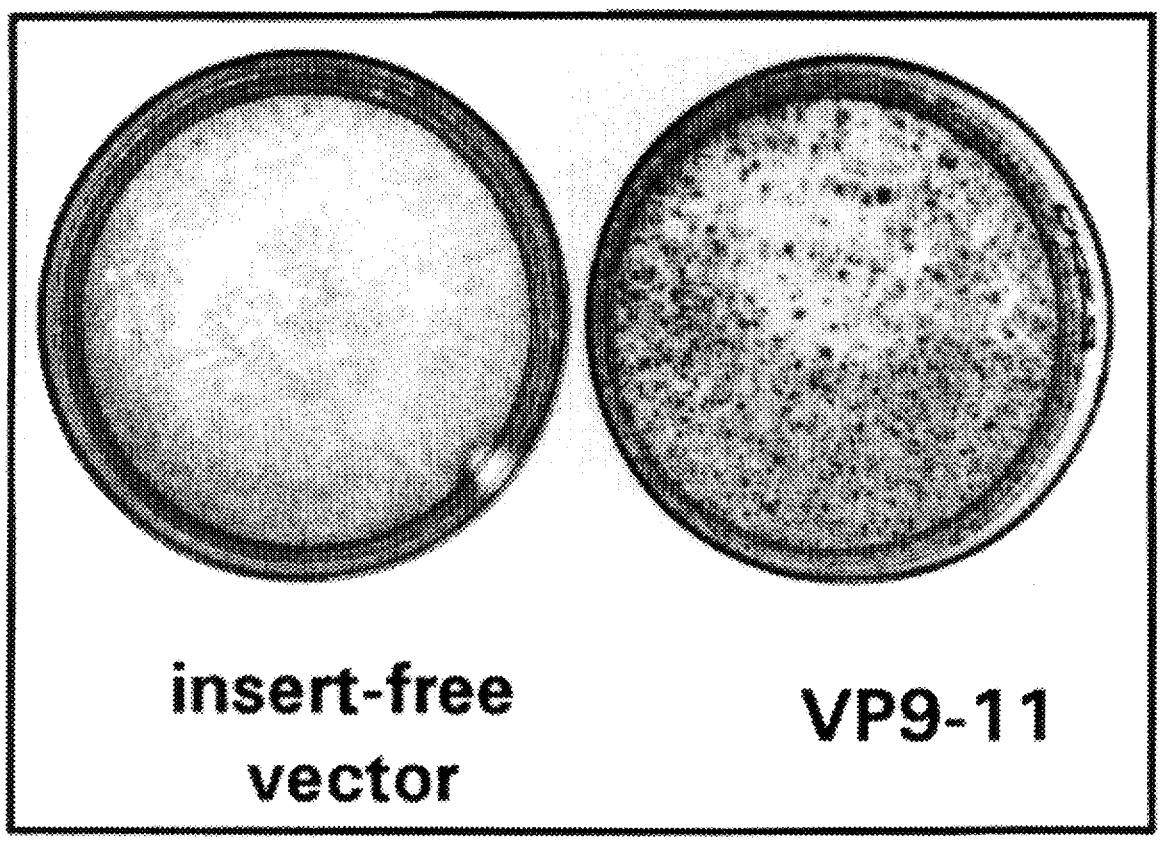
Figure 8A:
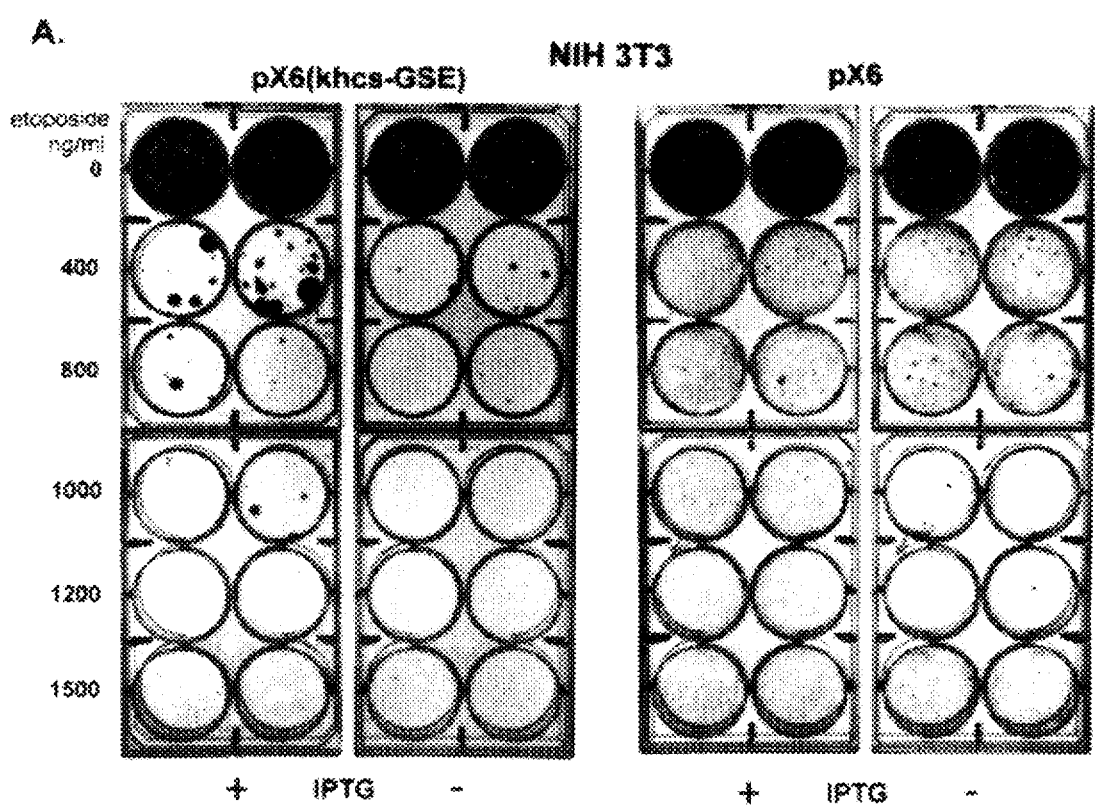
FIG. 8 shows resistance to various concentrations of etoposide, conferred upon the cells by the GSE anti-khcs under an IPTG-inducible promoter (Panel A) and the scheme for this selection (Panel B).
Figure 8B:
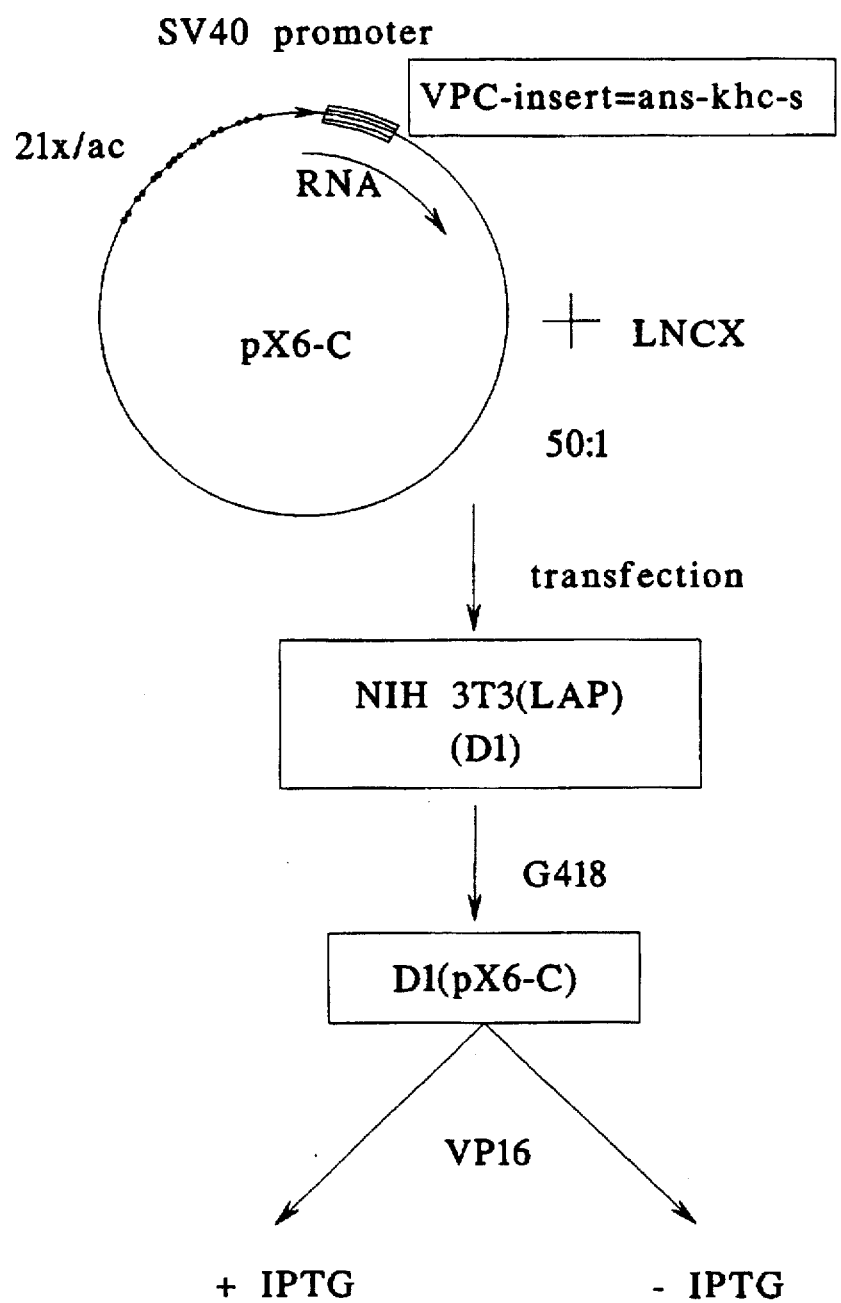
Figure 13A:
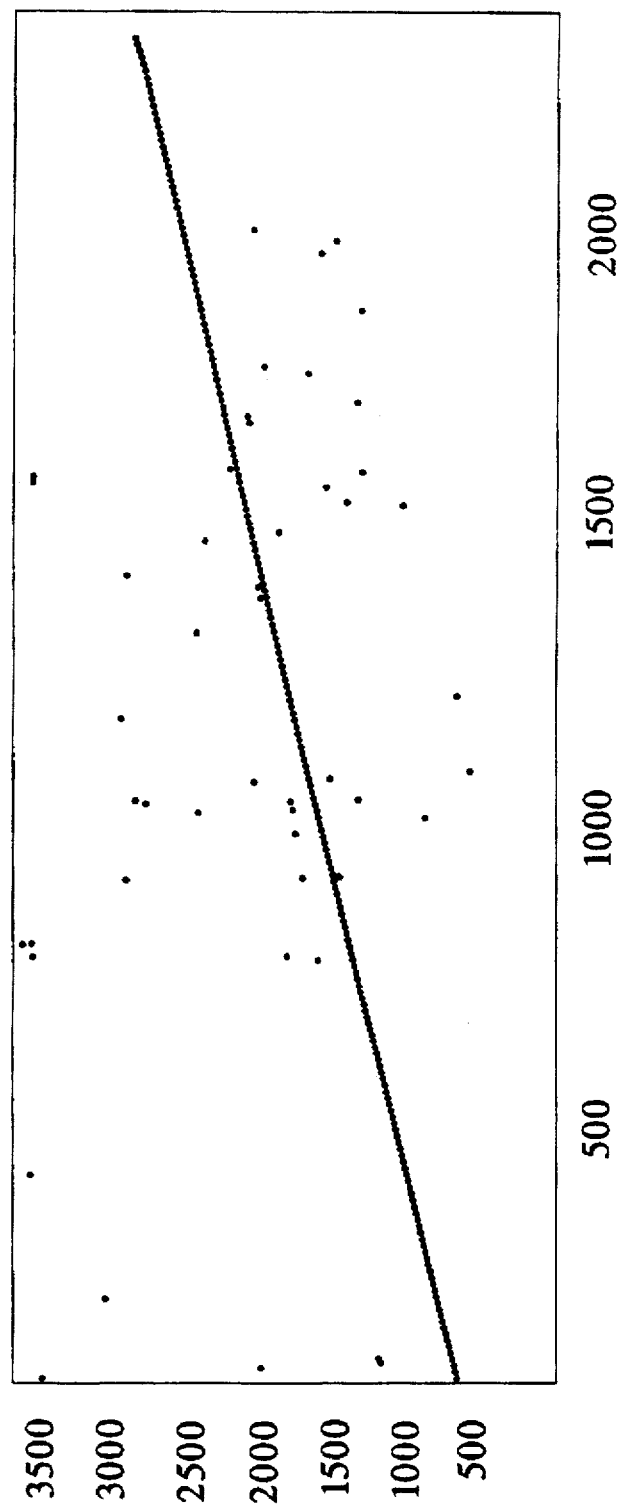
FIG. 13 shows the dot matrix alignments of khcs protein sequence deduced from the nucleotide sequence in FIG. 12 with kinesin heavy chain sequences from human (Panel A), mouse (Panel B), squid (Panel C) or the portion of mouse khcs encoded by the anti-khcs GSE (Panel D).
Figure 13B:
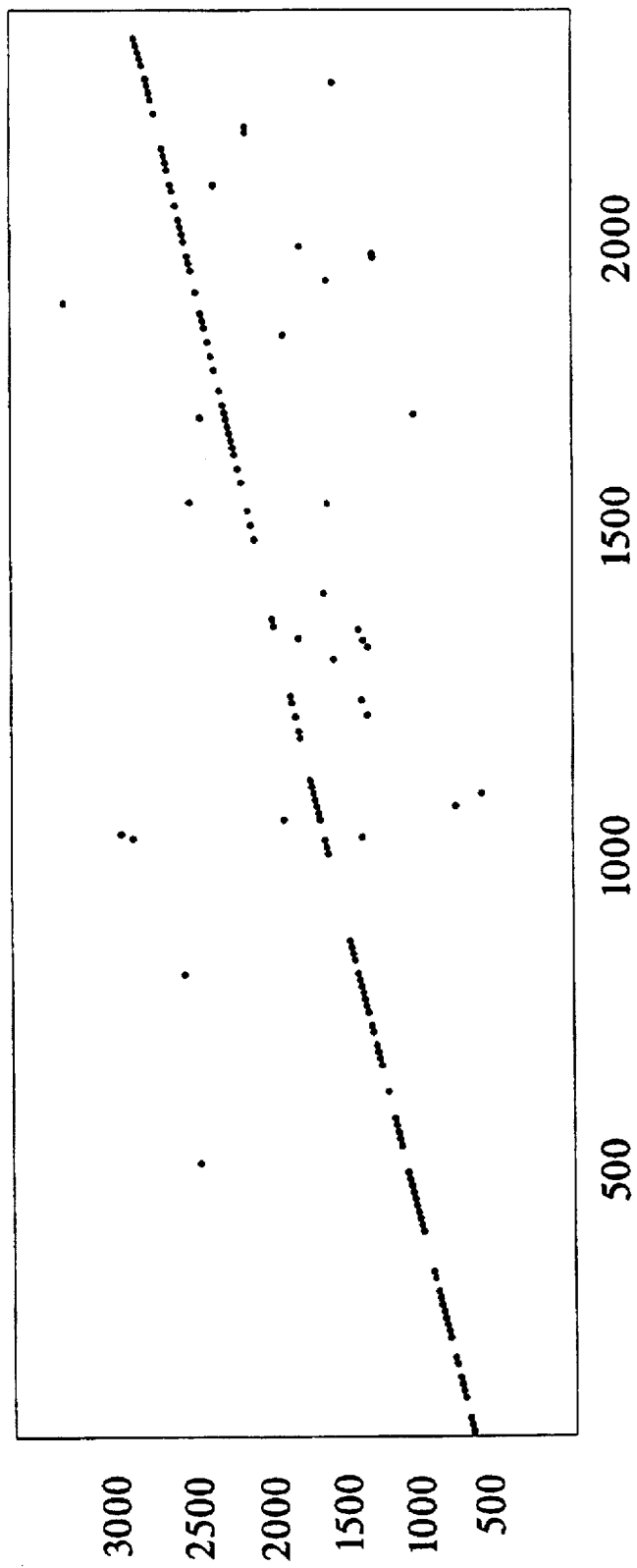
Figure 13C:
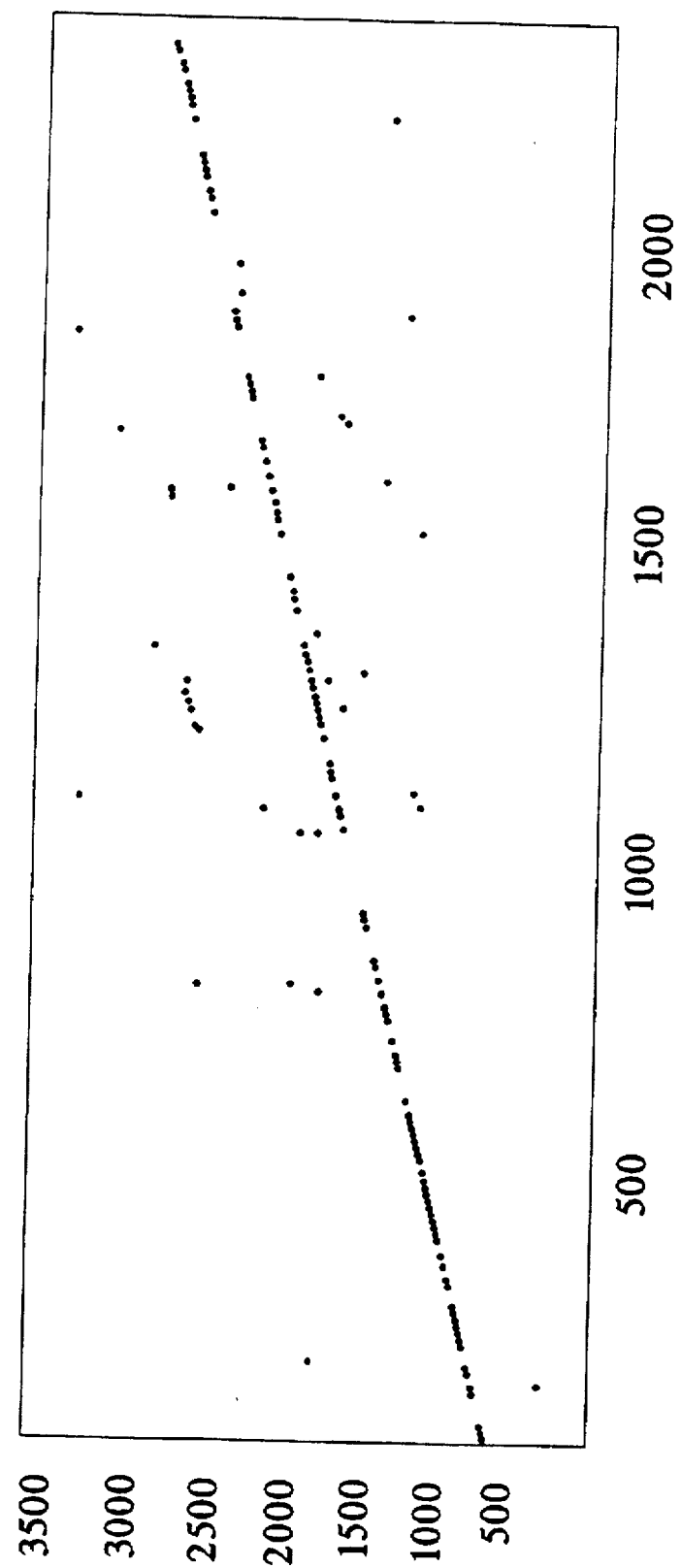
Figure 13D:
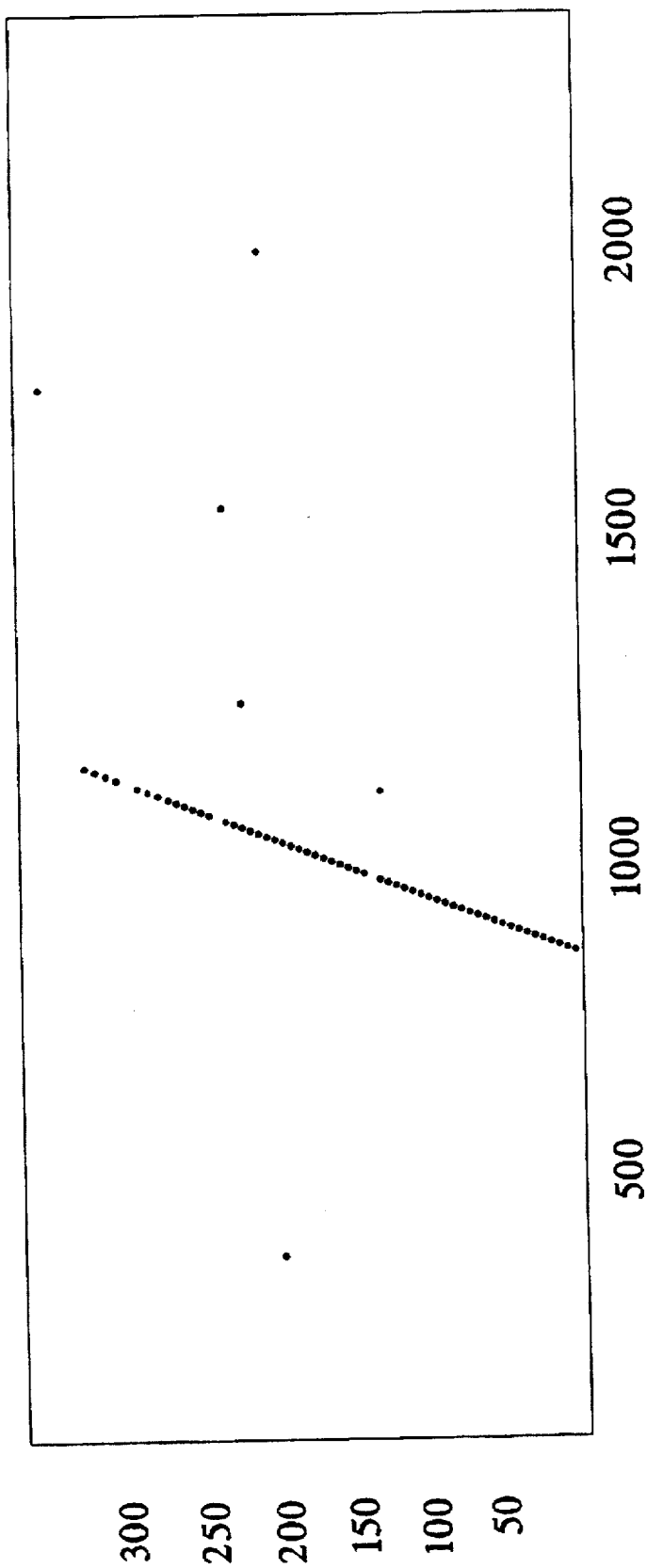
Figure 14A:
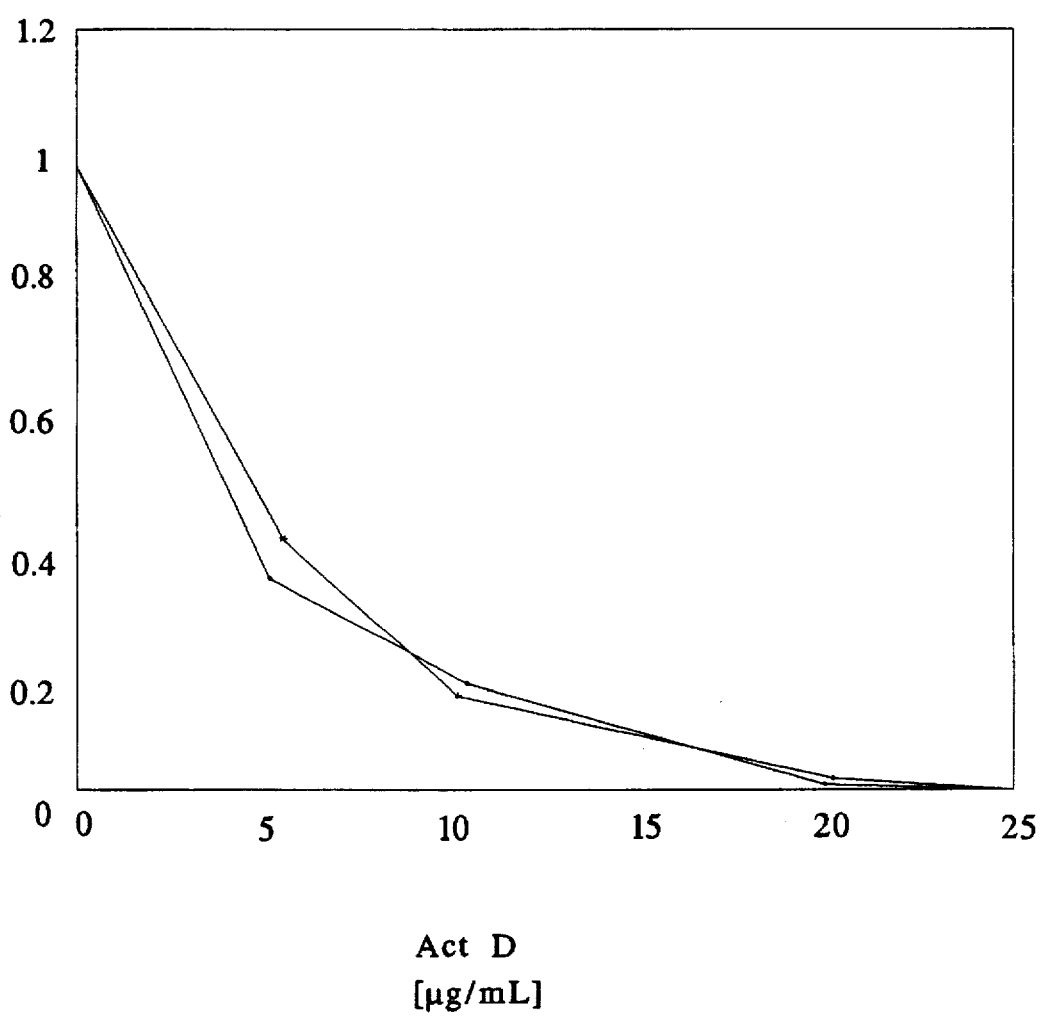
FIG. 14 shows the plating efficiency in the presence of various chemotherapeutic drugs of NIH 3T3 cells infected with the LNCX vector (indicated by crosses) or with the LNCX vector containing the anti-khcs GSE (indicated by dots).
Figure 14B:
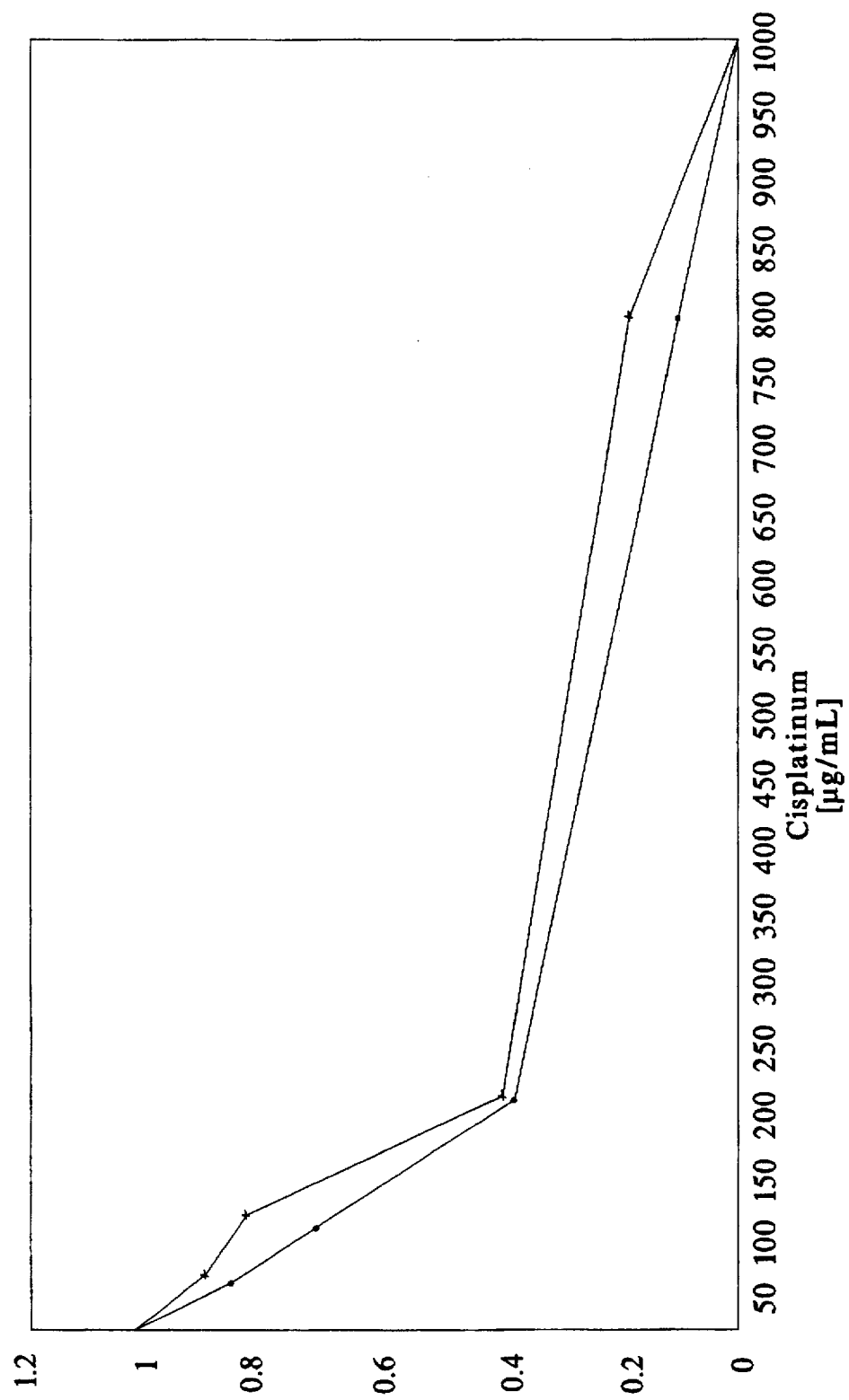
Figure 14C:
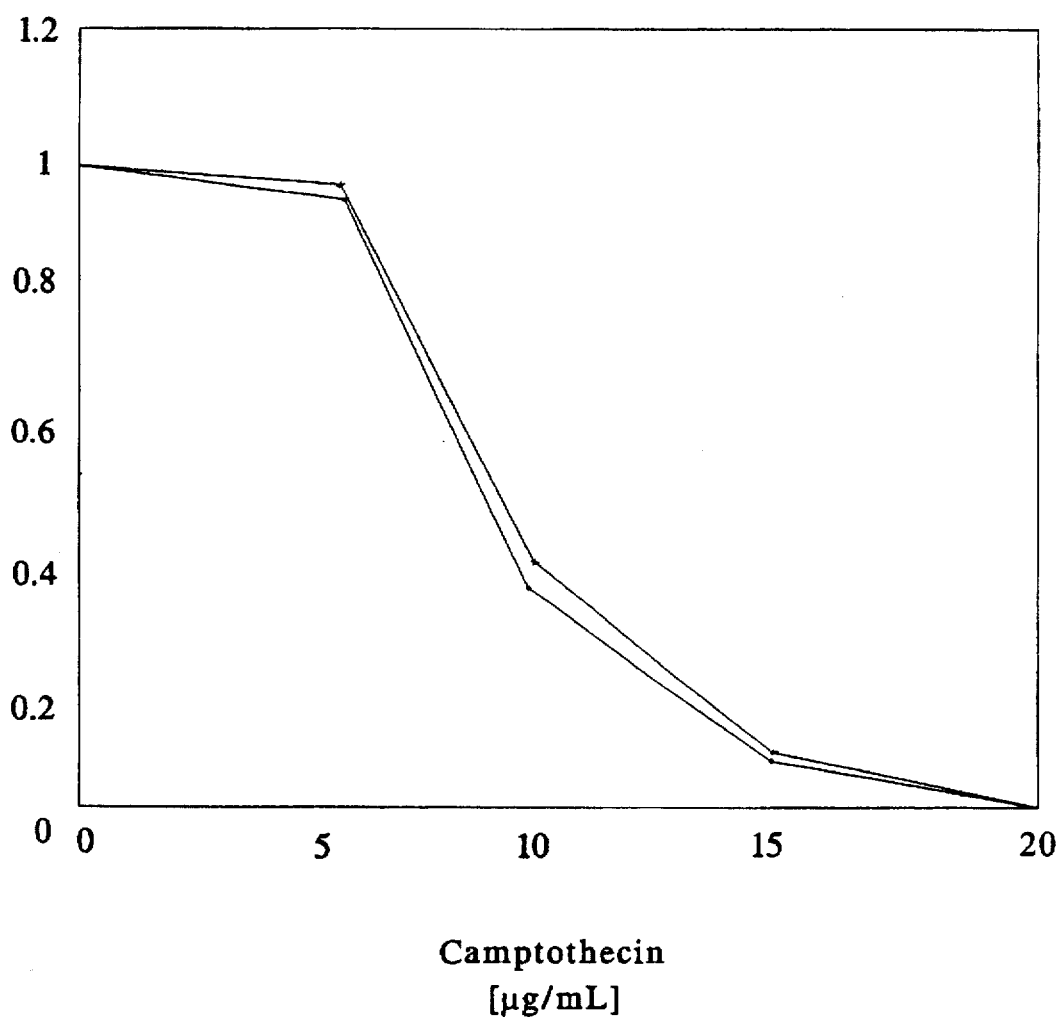
Figure 14D:
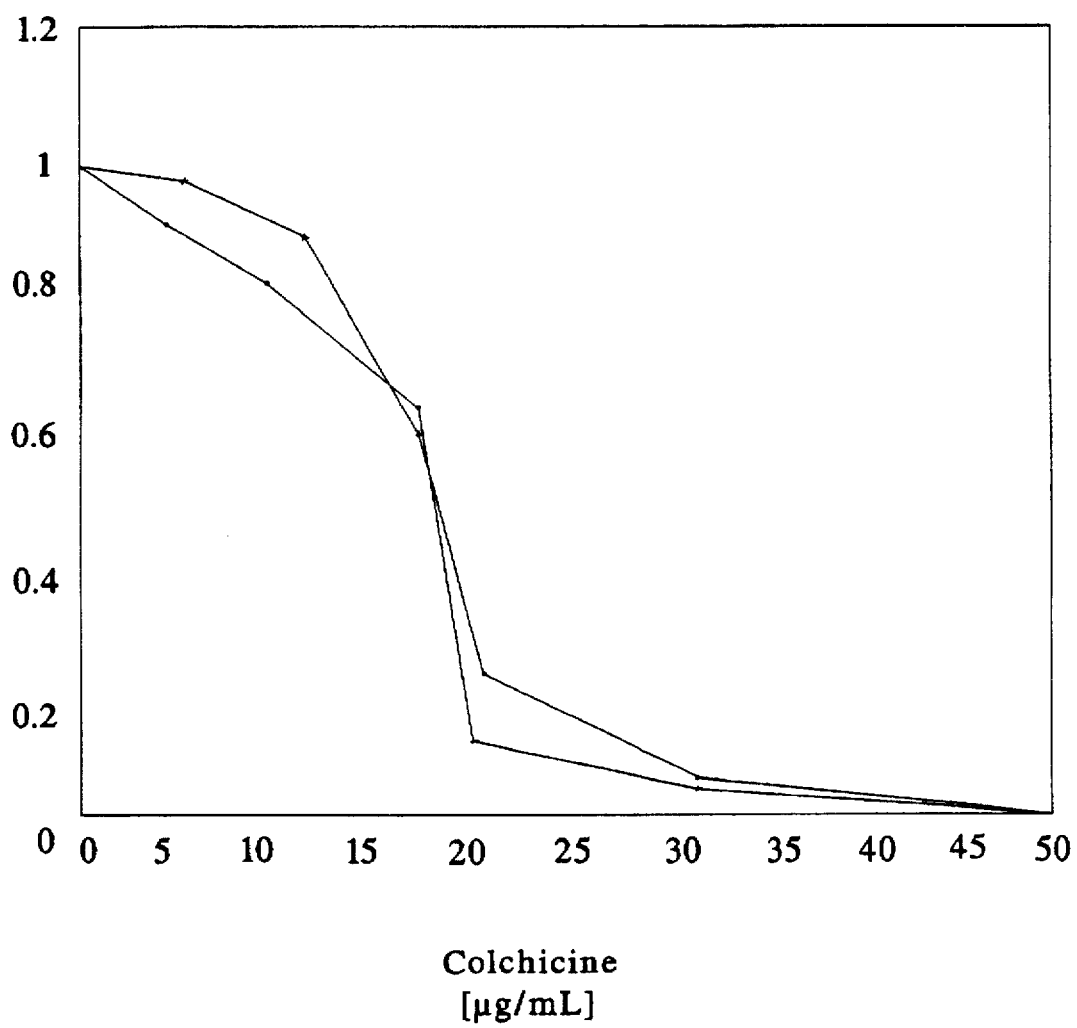
Figure 14E:
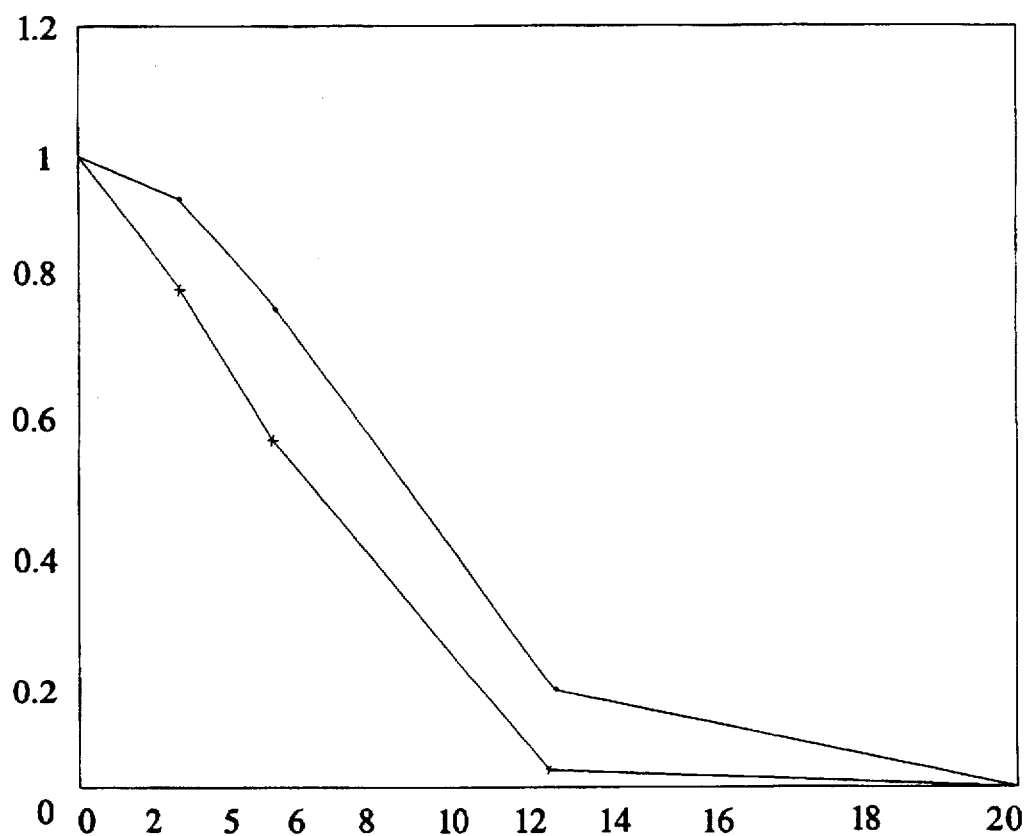
Figure 14F:
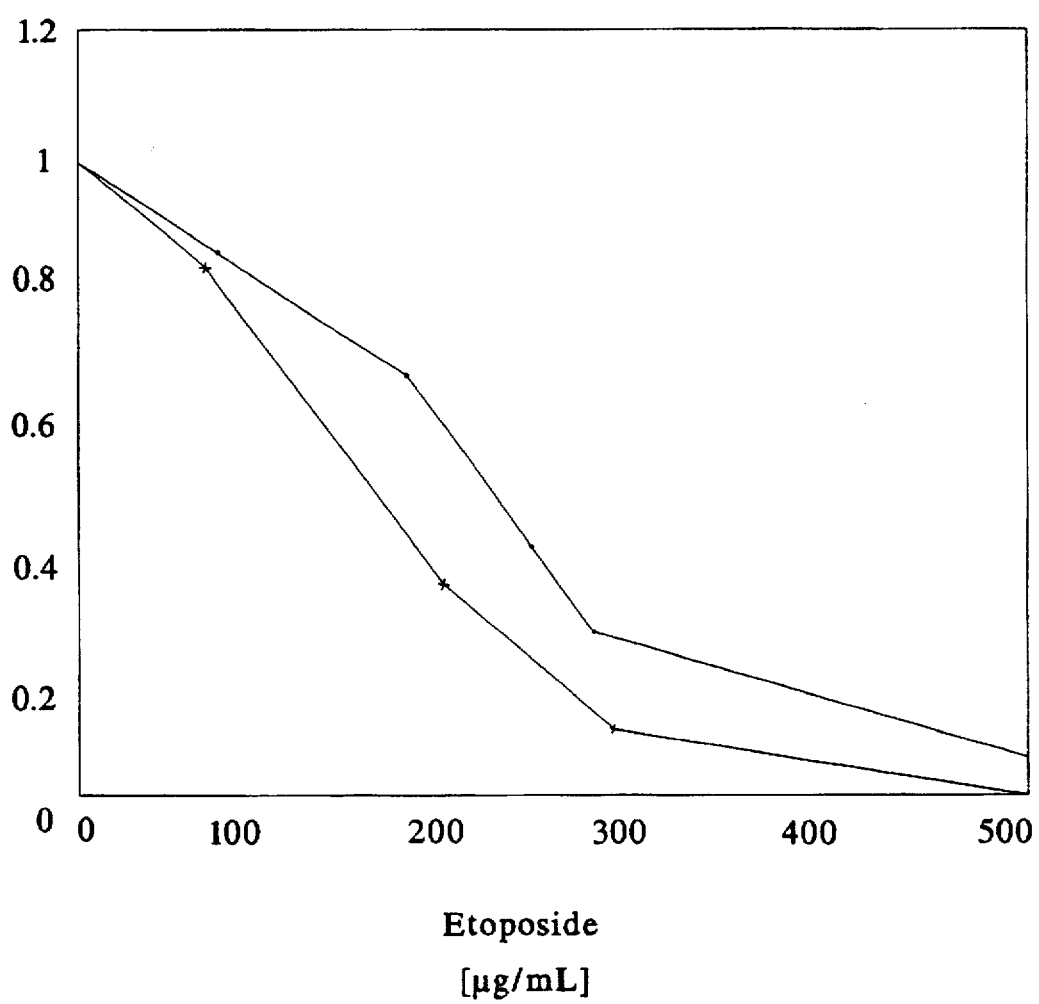

The proviral inserts contained in the etoposide-selected NIH 3T3 cells were analyzed by PCR. This analysis (see FIG. 5B) showed an enrichment the specific fragments, relative to the unselected population of the infected cells. Individual PCR-amplified fragments were recloned into the LNCX vector in the same position and orientation as in the original plasmid, as illustrated in FIG. 6. A total of 42 proviral inserts, enriched after etoposide selection, were thus recloned, and tested either in batches or individually for the ability to confer increased etoposide resistance after retroviral transduction into NIH 3T3 cells. Three non-identical clones were found to induce etoposide resistance, indicating that they contained biologically active GSEs. Etoposide resistance induced by these clones is illustrated in FIGS. 7 and 8. These GSEs were named anti-khcs, VPA and VP9-11.

The ability of one of these GSEs (anti-khcs) to induce etoposide resistance was further documented by using the isopropyl β-D-thiogalactopyranoside (IPTG)-inducible promoter/activator system, as described by Baim et al., Proc. Natl. Acad. Sci. USA 88:5072–5076 (1991). The components of this system include an enhancer-dependent promoter, combined in cis with multiple repeats of the bacterial lac operator, and a gene expressing LAP267, an artificial regulatory protein derived from the lac repressor and a mammalian transcriptional activator. The anti-khcs GSE was cloned into the plasmid pX6.CLN, which contains the inducible promotor used by Balm et al., supra. (a gift of Dr. T. Shenk) which expresses the inserts from an enhancer-less SV40 early gene promoter supplemented with 21 repeats of the lac operator sequence. The resulting plasmid, which contains no selectable markers, was co-transfected into NIH 3T3 cells together with the LNCX plasmid carrying the neo gene. The mass population of G418-selected transfectants, along with control cells transfected with the insert-free vector, was exposed to increasing concentrations of etoposide, in the presence or in the absence of 5 mM IPTG. Even though the co-transfection protocol usually leads to the integration of the GSE in only a fraction of the G418-resistant cells, transfection with anti-khcs resulted in a clearly increased etoposide resistance, which was dependent on IPTG (see FIG. 8).

EXAMPLE 5

Sequence Analysis Of GSEs Conferring Resistance To The Chemotherapeutic Drug Etoposide The GSEs anti-khcs, VPA, and VP9-11, cloned as described in Example 4, were sequenced by the standard dideoxy sequencing procedure, and the deduced sequences are shown in FIGS. 9–11. The nucleotide sequences of the "sense" and "antisense" strands, as well as amino acid sequences of the peptides encoded by these strands, were analyzed for homology to the nucleic acid and protein sequences present in the National Center for Biotechnology Information data base, using the BLAST network program for homology search. No significant homology with any sequence was detected for the GSEs VPA and VP9-11. In contrast, the sequence corresponding to the "antisense" strand of the anti-khcs GSE, showed strong homology with several genes encoding the heavy chain of kinesins, a family of microtubule motor proteins involved in intracellular movement of organelles or macromolecules along the microtubules of eukaryotic cells. This protein family has been reviewed by Endow, Trends Biochem. Sci. 16:221–225 (1991). The highest homology was found with the human kinesin heavy chain (KHC) gene, as described by Navone et al., J. Cell Biol. 117:1263–1275 (1992). Anti-khcs therefore encodes antisense RNA for a mouse khc gene, which we term khcs for khc associated with sensitivity (to drugs) or senescence. We refer to the kinesin molecule, formed by the association of the Khcs protein with kinesin light chains, as kinesin-S, to distinguish it from the other kinesins present in mammalian cells. These results demonstrate that chemotherapeutic drug selection for GSEs can lead to the discovery of novel genetic elements, and can also reveal roles of genes in drug sensitivity that had never before been suspected.

EXAMPLE 6

Cloning And Analysis Of The Gene From Which Anti-khcs GSE Gene Was Derived

The anti-khcs GSE isolated in Example 4 was used as a probe to screen 400,000 clones from each of two cDNA libraries in the lambda gt10 vector. These libraries were prepared by conventional procedures from the RNA of mouse BALB/c 3T3 cells, either unsynchronized or at G0→G1 transition, as described by Lan and Nathans, EMBO J. 4:3145–3151 (1985) and Proc. Natl. Acad. Sci. USA 84:1182–1186 (1987) (a gift of Dr. L. Lau). Screening of the first library yielded no hybridizing clones, but two different clones from the second library were found to contain anti-khcs sequences. These clones were purified and sequenced. Sequence analysis showed that we have isolated the bulk of the mouse khcs cDNA, corresponding to 796 codons (the full-length human KHC cDNA encodes 963 amino acids). This sequence is shown in FIG. 12. The missing 5' and 3' terminal sequences are currently being isolated using the "anchored PCR" technique, as described by Ohara et al., Proc. Natl. Acad. Sci. USA 86:5673–5677 (1989).

The dot-matrix alignment of the sequenced portion of the khcs protein with previously cloned KHC proteins from the human (see Navone et al., J. Cell. Biol. 117: 1263–1275 (1992)), mouse (see Kato, J. Neurosci. 2:704–711 (1991)) and squid (see Kosik et al., J. Biol. Chem. 265:3278–3283 (1990)) is shown in FIG. 13. The portion corresponding to the anti-khcs GSE, is shown in FIG. 9. The khcs gene is most highly homologous to the human gene (97% amino acid identity), suggesting that the human KHC (KHCS) gene is functionally equivalent to the mouse khcs. The alignment also shows that the anti-khcs GSE corresponds to the region which is the most highly diverged between different kinesins. This result suggests that the anti-khcs GSE is an antisense-oriented GSE fragment with an inhibitory effect specific to kinesin-S and not to the other mouse kinesins. This suggests the possibility that suppression of the other members of the kinesin family would have a detrimental effect on cell growth, thus resulting in selective isolation of the most specific sequence within the khcs gene.

EXAMPLE 7

Assessment Of Drug Cross-Resistance Conferred By Resistance To Etoposide

To determine the spectrum of drugs to which the anti-khcs GSE would confer resistance, we have developed a stable population of ecotropic packaging cells producing the LNCX virus with the anti-khcs insert. This virus was used to infect NIH 3T3 cells. Two days after infection, the cells were analyzed for resistance to several different drugs, relative to control cells infected with the LNCX vector virus, using the standard plating efficiency assay. FIG. 14 shows one out of three sets of experiments carried out with different drugs by this assay. Cells infected with the anti-khcs virus showed a clear increase in their resistance to etoposide and Adriamycin relative to control NIH 3T3 cells infected with the control LNCX virus. No changes in resistance were observed with colchicine, cisplatin, camptothecin, or actinomycin D. These latter results remain preliminary, however, because this assay, analyzing total unselected virus-infected populations is relatively insensitive, compared with analysis of highly expressing individually-selected clones. Overall, these results demonstrate that selection of GSEs that confer resistance to one chemotherapeutic drug can result in obtaining GSEs that confer resistance to additional chemotherapeutic drugs.

EXAMPLE 8

Assessment Of Cellular Effects Of GSEs That Confer Resistance To Etoposide

Figure 15:
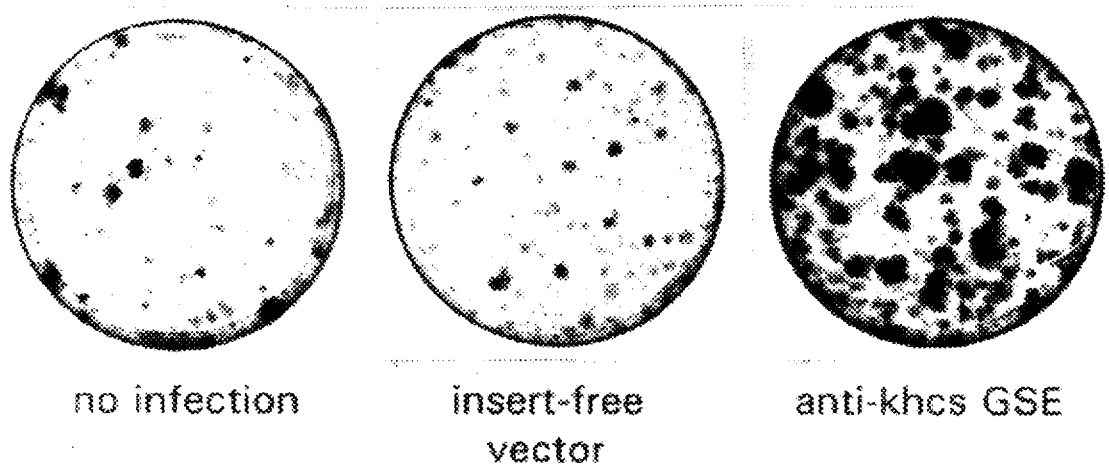
FIG. 15 demonstrates increased immortalization of primary mouse embryo fibroblasts by infection with the LNCX vector containing the anti-khcs GSE, relative to cells infected with the LNCX vector alone or uninfected (control) cells.

The virus carrying the anti-khcs GSE was tested for the ability to increase the life span of primary mouse embryo fibroblasts (MEF). MEF were prepared from 10 day old mouse embryos by a standard trypsinization procedure and senescent cells were frozen at different passages prior to crisis. Senescent MEF, two weeks before crisis, were infected with recombinant retroviruses carrying LNCX vector either without an insert or with anti-khcs. FIG. 15 shows MEF cell colonies two weeks after crisis. Relative to uninfected MEF cells, or cells infected with a control LNCX virus, cells infected with anti-khcs showed a great increase in the proportion of cells surviving the crisis. Post-crisis cells infected with the anti-khcs virus showed no microscopically visible features of neoplastic transformation. These results indicate that anti-khcs promotes the immortalization of normal senescent fibroblasts. These results suggest that the normal function of kinesin-S may be associated with the induction of programmed cell death occurring after exposure to certain cytotoxic drugs or in the course of cellular senescence. These results also indicate that isolation of GSEs that confer resistance to chemotherapeutic drugs can provide insight into the cellular genes and processes involved in cell growth regulation.

EXAMPLE 9

Assessment Of The Role Of Decreased khcs Gene Expression In Naturally Occurring Mechanisms Of Drug Resistance To test whether decreased khcs gene expression is associated with any naturally occurring mechanisms of drug resistance, an assay was developed for measuring khcs mRNA levels by cDNA-PCR. This assay is a modification of the quantitative assay described by Noonan et al., Proc. Natl. Acad. Sci. USA 87:7160–7164 (1990) for determining mdr-1 gene expression. The oligonucleotide primers had the sequences AGTGGCTGGAAAAC-GAGCTA [SEQ. ID. No. 19] and CTTGATCCCTTCTGGTTGAT [SEQ. ID. No. 20]. These primers were used to amplify a 327 bp segment of mouse khcs cDNA, corresponding to the anti-khcs GSE. These primers efficiently amplified the mouse cDNA template but not the genomic DNA, indicating that they spanned at least one intron in the genomic DNA. Using these primers, we determined that khcs mRNA is expressed at a higher level in the mouse muscle tissue than in the kidney, liver or spleen.

Figure 16:
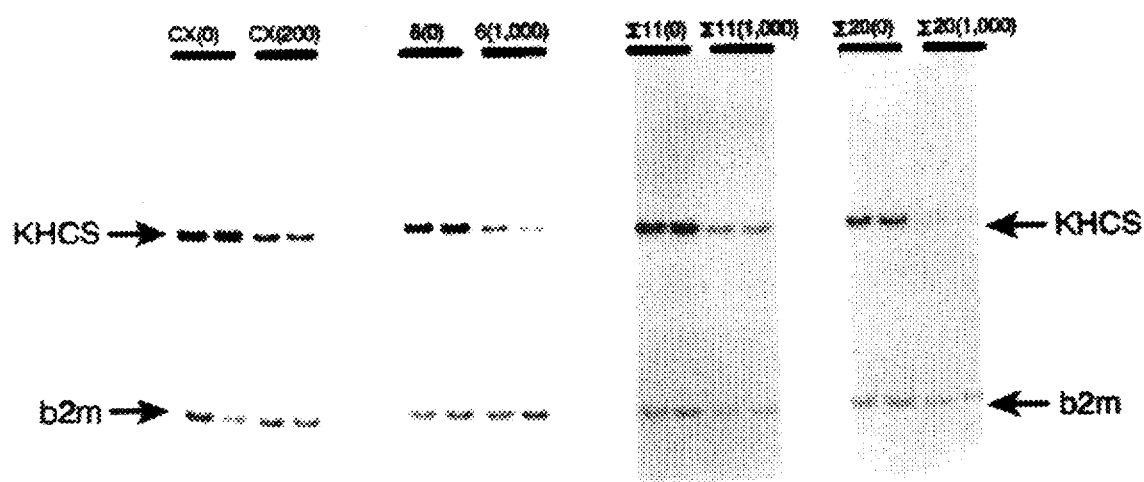
FIG. 16 shows cDNA-PCR quantitative analysis of expression of the human khcs gene in various unselected and etoposide-selected human HeLa cells. Lanes a shows results for clone CX(O), lands a' for clone CX(200), lanes b for clone Σ11(O), lanes b' for clone Σ11 (1000), lanes c for clone 6(O), lanes c' for clone 6(1000), lanes d for clone Σ20(O) and lanes d' for clone Σ20 (1000). The numbers in parentheses for each clone name indicate the concentration of etoposide (ng/ml) present in the growth media. Bands indicative of khcs expression are shown along with bands for β-2 microglobulin expression as an internal control.

In another experiment a pair of primers amplifying a homologous segment of the human KHCS cDNA was selected, based on the reported human KHC sequence published by Navone et al., J. Cell. Biol. 117:1263–1275 (1992). The sequences of these primers are AGTGGCTTGAAAAT-GAGCTC [SEQ. ID. No. 21] and CTTGATCCCTTCTGG-TAGATG [SEQ: ID. No. 22], and they amplify a 327 bp cDNA fragment. These primers were used to test for changes in the KHCS gene expression in several independently isolated populations of human HeLa cells, each selected for spontaneously acquired etoposide resistance. $\beta_2$-microglobulin cDNA sequences were amplified as an internal control. FIG. 16 shows the results of the cDNA-PCR assay on the following populations: CX(0), HeLa population infected with the LNCX vector virus and selected with G418; CX (200), the same cells selected for resistance to 200 ng/ml etoposide; Σ11(0), 6(0) and Σ21(0), populations obtained after infection of HeLa cells with recombinant retroviruses carrying different GSEs derived from topoisomerase α cDNA, as described in Example 1, and selected with G418: Σ11(1000), 6(1000) and Σ21(1000), the same populations selected for resistance to 1 μg/ml etoposide. As shown in FIG. 16, the yield of the PCR product specific for the khcs gene was significantly lower in each of the etoposide-selected populations than in the control cells. This result indicates that a decrease in the khcs gene expression is a common natural mechanism for drug resistance.

We claim:

1. A method of identifying genetic suppressor elements (GSEs) that confer a selectable phenotype upon a eukaryotic cell, the method comprising the steps of:
   (a) synthesizing randomly fragmented cDNA from the total mRNA of a eukaryotic cell to yield DNA fragments having a size of less than about 700 basepairs;
   (b) transferring the DNA fragments to an expression vector to yield a library, wherein each of the DNA fragments is operatively linked to a protein translation initiation codon, and wherein the expression vector which expresses the DNA fragments in a living eukaryotic cell that which exhibits the selectable phenotype;
   (c) genetically modifying living eukaryotic cells by introducing the genetic suppressor element library into the cells;
   (d) isolating or enriching for genetically modified living eukaryotic cells containing genetic suppressor elements which centers the selectable phenotype by selecting cells that express the selectable phenotype, and;
   (e) obtaining the genetic suppressor elements from the genetically modified cells.

2. A genetic suppressor element identified by the method of claim 1.

3. A genetic suppressor element according to claim 2 having a nucleotide sequence that is homologous to a portion of the human or mouse khcs gene.

4. A mammalian cell that expresses a GSE according to claim 3.

5. A method of overcoming in vitro drug resistance in a cancer cell, comprising the step of expressing the cancer cell a complete gene to which a GSE according to claim 3 is homologous.

6. A genetic suppressor element according to claim 2 having a nucleotide sequence that is homologous to a portion of a gene comprising the nucleotide sequence shown in FIG. 10.

7. A mammalian cell that expresses a GSE according to claim 6.

8. A method of overcoming in vitro drug resistance in a cancer cell, comprising the step of expressing in the cancer cell a complete gene to which a GSE according to claim 6 is homologous.

9. A genetic suppressor element according to claim 2 having a nucleotide sequence that is homologous to a portion of a gene comprising the nucleotide sequence shown in FIG. 11.

10. A mammalian cell that expresses a GSE according to claim 9.

11. A method of overcoming in vitro drug resistance in a cancer cell, comprising the step of expressing in the cancer cell a complete gene to which a GSE according to claim 9 is homologous.

12. A genetic suppressor element according to claim 2 having a nucleotide sequence that is homologous to the nucleotide sequence or its complement shown in FIG. 9.

13. A mammalian cell that expresses a GSE according to claim 12.

14. A genetic suppressor element according to claim 2 having a nucleotide sequence that is homologous to the nucleotide sequence shown in FIG. 10 or its complement.

15. A mammalian cell that expresses a GSE according to claim 14.

16. A genetic suppressor element according to claim 2 having a nucleotide sequence that is homologous to the nucleotide sequence shown in FIG. 11 or its complement.

17. A mammalian cell that expresses a GSE according to claim 16.

18. A mammalian cell that expresses a GSE according to claim 2.

19. A method according to claim 1, wherein the genetic suppressor element is a sense oriented genetic suppressor element encoding a peptide.

20. A method according to claim 1, wherein the genetic suppressor element is an antisense-oriented genetic suppressor element encoding an antisense RNA.

21. A synthetic oligonucleotide having a nucleotide sequence from about 12 nucleotides to all of the nucleotide sequence of the antisense RNA encoded by the GSE produced by claim 20.

22. The method of claim 1, wherein the selectable phenotype is resistance to a chemotherapeutic drug.

23. The method of claim 1, wherein the expression vector is a retroviral vector.

24. The method of claim 1, wherein the library is a normalized library.

25. A method of identifying GSEs corresponding to genes that when suppressed by GSEs, confer a selectable phenotype upon a eukaryotic cell having such suppressed genes, the method comprising the steps of:

(a) obtaining a total mRNA population from a eukaryotic cell;

(b) synthesizing randomly fragmented cDNA from the total mRNA to yield random cDNA fragments having a size less than about 700 basepairs;

(c) ligating the random cDNA fragments to synthetic adaptors to produce amplifiable random cDNA fragments;

(d) amplifying the random cDNA fragments;

(e) cloning the amplified mixture of random cDNA fragments into a suitable expression vector to produce a random fragment expression library, wherein each of the random cDNA fragments is operatively linked to a protein translation initiation codon;

(f) transferring the random fragment expression library into appropriate target eukaryotic cells;

(g) isolating or enriching for genetically modified living cells containing a selectable phenotype-conferring genetic suppressor elements by identifying and isolating or enriching for those cells that express the selectable phenotype; and (h) recovering the GSE from the target cell having the selectable phenotype.

26. A synthetic oligonucleotide having a nucleotide sequence that corresponds to from about 12 nucleotides to all of the nucleotide sequence of an antisense RNA encoded by a GSE produced by the method claim 25.

27. A genetic suppressor element identified by the method of claim 25.

28. A genetic suppressor element according to claim 27 having a nucleotide sequence that is homologous to a portion of the human or mouse khcs gene.

29. A genetic suppressor element according to claim 27 having a nucleotide sequence that is homologous to a portion of a gene comprising the nucleotide sequence shown in FIG. 10.

30. A genetic suppressor element according to claim 27 having a nucleotide sequence that is homologous to a portion of a gene comprising the nucleotide sequence shown in FIG. 11.

31. A genetic suppressor element according to claim 27 having a nucleotide sequence that is homologous to the nucleotide sequence shown in FIG. 9 or its complement.

32. A genetic suppressor element according to claim 27 having a nucleotide sequence that is homologous to the nucleotide sequence shown in FIG. 10 or its complement.

33. A genetic suppressor element according to claim 27 having a nucleotide sequence that is homologous to the nucleotide sequence shown in FIG. 11 or its complement.

34. A mammalian cell that expresses a GSE according to claim 27.

35. The genetic suppressor element according to claim 27, wherein the genetic suppressor element is a sense-oriented genetic suppressor element encoding a peptide.

36. The genetic suppressor element according to claim 27, wherein the genetic suppressor element is an antisense-oriented genetic suppressor element encoding an antisense RNA.

37. The method of claim 25, wherein the selectable phenotype is resistance to a chemotherapeutic drug.

38. The method of claim 25, wherein the expression vector is a retroviral vector.

39. The method of claim 25, wherein the library is a normalized library.

40. A method for identifying GSEs corresponding to genes that, when suppressed by GSE, confer a selectable phenotype upon a eukaryotic cell having such suppressed genes, the method comprising the steps of:

(a) obtaining genomic DNA from a eukaryotic cell;

(b) randomly fragmenting the genomic DNA to produce random genomic DNA fragments having a size less than about 700 basepairs;

(c) ligating the random genomic DNA fragments to synthetic adaptors to produce amplifiable random genomic DNA fragments;

(d) amplifying the random genomic DNA fragments;

(e) cloning the amplified mixture of random genomic DNA fragments into a suitable expression vector to produce a random fragment expression library, wherein each of the random genomic DNA fragments is operatively linked to a protein translation initiation codon;

(f) transferring the random fragment expression library into appropriate target eukaryotic cells;

(g) isolating or enriching for genetically modified living cells containing a selectable phenotype-conferring genetic suppressor element by identifying and isolating or enriching for those cells that express the selectable phenotype; and (h) recovering the GSE from the target cell having the selectable phenotype.

41. A synthetic oligonucleotide having a nucleotide sequence that corresponds to from about 12 nucleotides to all of the nucleotide sequence of an antisense RNA encoded by a GSE produced by the method of claim 40.

42. The method of claim 40, wherein the expression vector is a retroviral vector.

43. The method of claim 40, wherein the expression vector is a retroviral vector.

44. A genetic suppressor element identified by the method of claim 40.

45. The genetic suppressor element according to claim 44, wherein the genetic suppressor element is a sense-oriented genetic suppressor element encoding a peptide.

46. A genetic suppressor element according to claim 44 having a nucleotide sequence that is homologous to a portion of the human or mouse khcs gene.

47. A genetic suppressor element according to claim 44 having a nucleotide sequence that is homologous to a portion of a gene comprising the nucleotide sequence shown in FIG. 10.

48. A genetic suppressor element according to claim 44 having a nucleotide sequence that is homologous to a portion of a gene comprising the nucleotide sequence shown in FIG. 11.

49. A genetic suppressor element according to claim 44 having a nucleotide sequence that is homologous to the nucleotide sequence or its complement shown in FIG. 9.

50. A genetic suppressor element according to claim 44 having a nucleotide sequence that is homologous to the nucleotide sequence shown in FIG. 10 or its complement.

51. A genetic suppressor element according to claim 44 having a nucleotide sequence that is homologous to the nucleotide sequence shown in FIG. 11 or its complement.

52. A mammalian cell that expresses a GSE according to claim 44.

53. The genetic suppressor element according to claim 44, wherein the genetic suppressor element is an antisense-oriented genetic suppressor element encoding an antisense RNA.

54. A genetic suppressor element identified by the method of claim 22.

55. A method of isolating a gene associated with sensitivity to chemotherapeutic drugs, comprising the step of screening a cDNA library with an oligonucleotide or polynucleotide having a nucleotide sequence of from about 12 to all of the nucleotides of the GSE according to claim 54.

56. A cloned gene isolated by the method of claim 55.

57. A method of isolating a gene associated with sensitivity to chemotherapeutic drugs, comprising the step of screening a genomic library with an oligonucleotide or polynucleotide having a nucleotide sequence of from about 12 to all of the nucleotides of the GSE according to claim 54.

58. A cloned gene isolated by the method of claim 57.

59. A diagnostic assay for chemotherapeutic drug resistance comprising the step of comparing the gene expression of a gene comprising a nucleotide sequence homologous to that of the GSE according to claim 54 in a cell to gene expression in a cell which is not drug resistant, wherein underexpression indicates chemotherapeutic drug resistance.

60. A method of overcoming in vitro drug resistance in a cancer cell, comprising the step of expressing in the cancer cell a complete gene to which a GSE according to claim 54 is homologous.

61. A genetic suppressor element identified by the method of claim 37.

62. A method of isolating a gene associated with sensitivity to chemotherapeutic drugs, comprising the step of screening a cDNA library with an oligonucleotide or polynucleotide having a nucleotide sequence of from about 12 to all of the nucleotides of the GSE according to claim 61.

63. A cloned gene isolated by the method of claim 62.

64. A method of isolating a gene associated with sensitivity to chemotherapeutic drugs, comprising the step of screening a genomic library with a oligonucleotide or polynucleotide having a nucleotide sequence of from about 12 to all of the nucleotides of the GSE according to claim 61.

65. A cloned gene isolated by the method of claim 64.

66. A diagnostic assay for chemotherapeutic drug resistance comprising the step of comparing the gene expression of a gene comprising a nucleotide sequence homologous to that of the GSE according to claim 61 in a cell to gene expression in a cell which is not drug resistant, wherein underexpression indicates chemotherapeutic drug resistance.

67. A method of overcoming in vitro drug resistance in a cancer cell, comprising the step of expressing in the cancer cell a complete gene to which a GSE according to claim 61 is homologous.

68. A genetic suppressor element identified by the method of claim 42.

69. A method of isolating a gene associated with sensitivity to chemotherapeutic drugs, comprising the step of screening a cDNA library with an oligonucleotide or polynucleotide having a nucleotide sequence of from about 12 to all of the nucleotides of the GSE according to claim 68.

70. A cloned gene isolated by the method of claim 69.

71. A method of isolating a gene associated with sensitivity to chemotherapeutic drugs, comprising the step of screening a genomic library with an oligonucleotide or polynucleotide having a nucleotide sequence of from about 12 to all of the nucleotides of the GSE according to claim 68.

72. A cloned gene isolated by the method of claim 71.

73. A diagnostic assay for chemotherapeutic drug resistance comprising the step of comparing the gene expression of a gene comprising a nucleotide sequence homologous to that of the GSE according to claim 68 in a cell to gene expression in a cell which is not drug resistant, wherein underexpression indicates chemotherapeutic drug resistance.

74. A method of overcoming in vitro drug resistance in a cancer cell, comprising the step of expressing in the cancer cell a complete gene to which a GSE according to claim 68 is homologous.

75. A method of identifying genetic suppressor elements that confer upon a eukaryotic cell resistance to one or more chemotherapeutic drugs, the method comprising the steps of:

(a) obtaining random DNA fragments of a gene associated with sensitivity to chemotherapeutic drugs having a size less than about 700 basepairs;

(b) transferring the DNA fragments to an expression vector to yield a library, wherein each of the random DNA fragments is operatively linked to a protein translation initiation codon, and wherein the expression vector is capable of expressing the DNA fragments in a living eukaryotic cell that is susceptible of inhibitory effects of a chemotherapeutic drug;

(c) genetically modifying living eukaryotic cells by introducing the genetic suppressor element library into the cells;

(d) isolating or enriching for genetically modified living cells containing a chemotherapeutic drug resistance-conferring genetic suppressor element by selecting cells in the presence of chemotherapeutic drug, and;

(e) obtaining a genetic suppressor element from the genetically modified eukaryotic cells.

76. The method of claim 75, wherein the cloned gene has a nucleotide sequence to which the GSE shown in FIG. 9 is homologous.

77. The method of claim 75, wherein the cloned gene has a nucleotide sequence to which the GSE shown in FIG. 10 is homologous.

78. The method of claim 75, wherein the cloned gene has a nucleotide sequence to which the GSE shown in FIG. 11 is homologous.

79. A GSE identified by the method of claim 75.

80. A GSE according to claim 79, having a nucleotide sequence selected from the group consisting of the nucleotide sequences shown in FIG. 1.

81. A GSE identified by the method of claim 76.

82. A GSE identified by the method of claim 77.

83. A GSE identified by the method of claim 78.

84. A mammalian cell that expresses a GSE according to claim 79.

85. A mammalian cell that expresses a GSE according to claim 81.

86. A mammalian cell that expresses a GSE according to claim 82.

87. A mammalian cell that expresses a GSE according to claim 83.

88. A synthetic oligonucleotide having a nucleotide sequence comprising from about 12 to all of the nucleotide sequence of a GSE according to claim 79.

89. A synthetic oligonucleotide having a nucleotide sequence comprising from about 12 to all of the nucleotide sequence of a GSE according to claim 81.

90. A synthetic oligonucleotide having a nucleotide sequence comprising from about 12 to all of the nucleotide sequence of a GSE according to claim 82.

91. A synthetic oligonucleotide having a nucleotide sequence comprising from about 12 to all of the nucleotide sequence of a GSE according to claim 83.

92. A normalized library of randomly fragmented cDNA corresponding to total mRNA expressed in a mammalian cell wherein each of the fragments does not exceed about 700 basepairs in length and wherein the random cDNA fragments are carried within a vector capable of expressing the fragments as a mRNA in a mammalian cell, each of the fragments being operatively linked to a translation initiation codon.

93. A library according to claim 92, wherein the expression vector is a retroviral vector.

* * * * *

UNITED STATES PATENT AND TRADEMARK OFFICE
CERTIFICATE OF CORRECTION

PATENT NO. : 5,665,550
DATED : September 9, 1997
INVENTOR(S): Roninson et al.

It is certified that error appears in the above-identified patent and that said Letters Patent is hereby corrected as shown below:

On the title page: Item [73]

IN THE ASSIGNEE:
Please replace "Chicago, Illinois" with --Urbana, Illinois--.

Item [63]

IN THE RELATED U.S. APPLICATION DATA:
Please insert --filed March 9, 1993, which is a continuation-in-part of an International Application-- after "33,086".

Item [56]

IN THE REFERENCES CITED, OTHER PUBLICATIONS:
Please replace "Sczakielet al." with Sczakielet et al."
Please replace "In vivo gene Transfer with Retroviral Vector-Producer Cels" with --In vivo gene Transfer with Retroviral Vector-Producer Cells--.

At col. 1, line 14, please insert the following:
-- This invention was made with government support under grants CA39365 and CA-56738 by the National Institutes of Health. The government has certain rights in the invention.--
At col. 1, line 62, please replace "; allowed September 9, 1992 with --, issued June 8, 1993--.
At col. 2, line 1, please replace "[in press as of filing date]" with --90: 3231-3235--.
At col. 2, line 33, please insert --drugs-- after "chemotherapeutic".
At col. 2, line 48, please replace "a drug resistance conferring" with --drug resistance conferring--.
At col. 3, line 12, please replace "FIG. 1" with --FIG. 1A through 1L--.
At col. 3, line 15, please insert --(RFEL)-- after "library".
At col. 3, line 16, please replace "(A)" with --FIG. 1A--.
At col. 3, line 17, please replace "(B)" with --FIG. 1B--.
At col. 3, line 17, please replace "(C)" with --FIG. 1C--.
At col. 3, line 18, please replace "(D)" with --FIG. 1D--.
At col. 3, line 18, please replace "(E)" with --FIG. 1E--.
At col. 3, line 19, please replace "(F)" with --FIG. 1F--.

UNITED STATES PATENT AND TRADEMARK OFFICE
CERTIFICATE OF CORRECTION

PATENT NO. : 5,665,550

DATED : September 9, 1997

INVENTOR(S) : Roninson et al.

It is certified that error appears in the above-identified patent and that said Letters Patent is hereby corrected as shown below:

At col. 3, line 19, please replace "(G)" with --FIG. 1G--.
At col. 3, line 20, please replace "(H)" with --FIG. 1H--.
At col. 3, line 20, please replace "(I)" with --FIG. 1I--.
At col. 3, line 21, please replace "(J)" with --FIG. 1J--.
At col. 3, line 21, please replace "(K)" with --FIG. 1K--.
At col. 3, , line 22, please replace "(L)" with --FIG. 1L--.
At col. 3, line 24, please replace "FIG. 2" with --Figures 2A and 2B--.
At col. 3, line 25, please replace "Panel A" with --FIG. 2A--.
At col. 3, line 26, please replace "Panel B" with --FIG. 2B--.
At col. 3, line 27, please replace "In this panel" with --In FIG. 2B--.
At col. 3, line 33, please replace "FIG. 3" with --Figures 3A and 3B--.
At col. 3, line 41, please replace "FIG. 5" with --Figures 5A and 5B--.
At col. 3, line 42, please replace "Panel A" with --FIG. 5A--.
At col. 3, line 43, please replace "Panel B" with --FIG. 5B--.
At col. 3, line 47, please replace "Figure 7" with --FIG. 7A and 7B--.
At col. 3, line 48, please replace "Panel A" with --FIG. 7A--.
At col. 3, line 49, please replace "Panel B" with --FIG. 7B--.
At col. 3, line 50, please replace "Figure 8" with --FIG. 8A and 8B--.
At col. 3, line 52, please replace "Panel A" with --FIG. 8A--.
At col. 3, line 53, please replace "Panel B" with --FIG. 8B--.
At col. 3, line 61, please replace "Figure 12" with --FIG. 12A through 12C--.
At col. 3, line 61, please replace "sequence of the most" with --sequence of most--.
At col. 3, line 63, please replace "Figure 13" with --FIG. 13A through 13D--.
At col. 3, line 64, please replace "Figure 12" with --FIG. 12A through 12C--.
At col. 3, line 65, please replace "Panel A" with --FIG. 13A--.
At col. 3, line 66, please replace "Panel B" with --FIG. 13B--.
At col. 3, line 66, please replace "Panel C" with --FIG. 13C--.
At col. 3, line 67, please replace "Panel D" with --FIG. 13D--.

UNITED STATES PATENT AND TRADEMARK OFFICE
CERTIFICATE OF CORRECTION

PATENT NO. : 5,665,550
DATED : September 9, 1997
INVENTOR(S) : Roninson et al

Page 3 of 4

It is certified that error appears in the above-identified patent and that said Letters Patent is hereby corrected as shown below:

At col. 4, line 1, please replace "Figure 14" with --FIG. 14A through 14F--.
At col. 4, line 14, please replace "lands a'" with --lanes a'--.
At col. 6, line 41, please replace "imunoglobulin" with --immunoglobulin--.
At col. 7, line 43, please replace "cotranfered" with --cotransferred--.
At col. 10, line 51, please replace "FIG. 1" with --FIG. 1A through 1L--.
At col. 11, line 34, please replace "FIG. 2" with --FIG. 2A and 2B--.
At col. 11, line 49, please replace "FIG. 3" with --FIG. 3B--.
At col. 12, line 6, please replace "FIG. 2" with --FIG. 2A and 2B--.
At col. 12, line 14, please replace "FIG. 2" with --FIG. 2A and 2B--.
At col. 12, line 23, please replace "FIG. 3" with --FIG. 3A--.
At col. 14, lines 3-4, please replace "FIG. 7 and 8" with --FIG. 7A and 7B and FIG. 8A and 8B--.
At col. 14, line 28, please replace "FIG. 8" with --FIG. 8A and 8B--.
At col. 15, line 4, please replace "Lan and Nathans" with --Lau and Nathans--.
At col. 15, line 22, please replace "FIG. 13" with --FIG. 13A through 13D--.
At col. 15, line 47, please replace "FIG. 14" with --FIG. 14A through 14F--.
At col. 16, line 67, please replace "topoisomerase a" with --topoisomerase II--.

UNITED STATES PATENT AND TRADEMARK OFFICE
CERTIFICATE OF CORRECTION

PATENT NO. : 5,665,550
DATED : September 9, 1997
INVENTOR(S) : Roninson et al

It is certified that error appears in the above-identified patent and that said Letters Patent is hereby corrected as shown below:

IN THE CLAIMS:
Please change the language of Claim 43 to recite:
43. The method of claim 40, wherein the library is a normalized library.'

Signed and Sealed this

Second Day of March, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.     : 5,665,550
DATED          : September 9, 1997
INVENTOR(S)    : Roninson et al.

It is certified that error appears in the above-identified patent and that said Letters Patent is hereby corrected as shown below:

Title page,
Item [73], Assignee, insert -- Board of Trustees of the University of Illinois, Urbana, Illinois --.

Signed and Sealed this

Twenty-eighth Day of February, 2006

JON W. DUDAS
*Director of the United States Patent and Trademark Office*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 164 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

```
GTGTCTGGGC GGAGCAAAAT ATGTTCCAAT TGTGTTTTCT TTTGATAGAT TCTTTCAACA        60

GACAGTCTTT TCTTAGCATC TTCATTTTTC TTTATTTTGT TGACTTGCAT ATTTTCATTT       120

ACAGGCTGCA ATGGTGACAC TTCCATGGTG ACGGTCGTGA AGGG                        164
```

( 2 ) INFORMATION FOR SEQ ID NO:2:

( i ) SEQUENCE CHARACTERISTICS:
        ( A ) LENGTH: 213 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

```
TGAAAAGATG TATGTCCCAG CTCTCATATT TGGACAGCTC CTAACTTCTA GTAACTATGA        60

TGATGATGAA AAGAAAGTGA CAGGTGGTCG AAATGGCTAT GGAGCCAAAT TGTGTAACAT       120

ATTCAGTACC AAATTTACTG TGGAAACAGC CAGTAGAGAA TACAAGAAAA TGTTCAAACA       180

GACATGGATG GATAATATGG GAAGAGCTGG TGA                                   213
```

( 2 ) INFORMATION FOR SEQ ID NO:3:

( i ) SEQUENCE CHARACTERISTICS:
        ( A ) LENGTH: 181 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

-continued

```
GCCCATTGGT CAGTTTGGTA CCAGGCTACA TGGTGGCAAG GATTCTGCTA GTCCACGATA      60

CATCTTTACA ATGCTCAGCT CTTTGGCTCG ATTGTTATTT CCACCAAAAC ATGATCACAC     120

GTTGAAGTTT TTATATGATG ACAACCAGCG TGTTGAGCCT GAATGGTACA TTCCTATTAT     180

T                                                                      181
```

( 2 ) INFORMATION FOR SEQ ID NO:4:

( i ) SEQUENCE CHARACTERISTICS:
    ( A ) LENGTH: 224 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

```
TGAATGGTAC ATTCCTATTA TTCCCATGGT GCTGATAAAT GGTGCTGAAG GAATCGGTAC      60

TGGGTGGTCC TGCAAAATCC CCAACTTTGA TGTGCGTGAA ATTGTAAATA ACATCAGGCG     120

TTTGATGGAT GGAGAAGAAC CTTTGCCAAT GCTTCCAAGT TACAAGAACT TCAAGGGTAC     180

TATTGAAGAA CTGGCTCCAA ATCAATATGT GATTAGTGGT GAAG                      224
```

( 2 ) INFORMATION FOR SEQ ID NO:5:

( i ) SEQUENCE CHARACTERISTICS:
    ( A ) LENGTH: 329 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

```
TGCGTGAAAT TGTAAATAAC ATCAGGCGTT TGATGGATGG AGAAGAACCT TTGCCAATGC      60

TTCCAAGTTA CAAGAACTTC AAGGGTACTA TTGAAGAACT GGCTCCAAAT CAATATGTGA     120

TTAGTGGTGA AGTAGCTATT CTTAATTCTA CAACCATTGA AATCTCAGAG CTTCCCGTCA     180

GAACATGGAC CCAGACATAC AAAGAACAAG TTCTAGAACC CATGTTGAAT GGCACCGAGA     240

AGACACCTCC TCTCATAACA GACTATAGGG AATACCATAC AGATACCACT GTGAAATTTG     300

TTGTGAAGAT GACTGAAGAA AAACTGGCA                                        329
```

( 2 ) INFORMATION FOR SEQ ID NO:6:

( i ) SEQUENCE CHARACTERISTICS:
    ( A ) LENGTH: 194 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:6:

```
CACTCTTTTC AGTTTCCTTT TCGTTGTCAC TCTCTTCATT TTCTTCTTCA TCTGGAACCT      60
```

-continued

```
TTTGCTGGGC TTCTTTCCAG GCCTTCACAG GATCCGAATC ATATCCCTC  TGAATCAGAA    120

CTTTAATTAA TTCTTTCTTA GGCTTATTTT CAATGATTAT TTGCCATCT  ATTTTCTCAT    180

AGATAAAGCG AGCC                                                      194
```

(2) INFORMATION FOR SEQ ID NO:7:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:7:

```
TCTGCCTCTG CTTTCATTTC TATGGTTATT CGTGGAATGA CTCTTTGACC ACGCGGAGAA    60

GGCAAAACTT CAGCCATTTG TGTTTTTTC  CCCTTGGCCT TCCCCCCTTT CCCAGGAAGT    120

CCGACTTGTT CATCTTGTTT TTCCTTGGCT TCAACAGCCT CCAATTCTTC AATAAATGTA    180

GCCAAGTCTT CTTTCCACAA ATCTGA                                         206
```

(2) INFORMATION FOR SEQ ID NO:8:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

```
GACACGACAC TTTTCTGTGG TTTCAGTTCT TTGTTACTAA GTTTGGGGA  AGTTTTGGTC    60

TTAGGTGGAC TAGCATCTGA TGGACAAAA  TCTTCATCAT CAGTTTTTTC ATCAAAATCT    120

GAGAAATCTT CATCTGAATC CAAATCCATT GTGAATTTTG TTTTGTTGC  TGCTCTCCGT    180

GGCTCTGTTT CTCG                                                      194
```

(2) INFORMATION FOR SEQ ID NO:9:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

```
CTGAAACCAC AGAAAAGTGT CGTGTCAGAC CTTGAAGCTG ATGATGTTAA GGGCAGTGTA    60

CCACTGTCTT CAAGCCCTCC TGCTACACAT TTCCCAGATG AAACTGAAAT TACAAACCCA    120

GTTCCTAAAA AGAATGTGAC AGTGAAGAAG ACAGCAGCAA AAAGTCAGTC TTCCACCTCC    180
```

| ACTACCGGTG | CCAAAAAAAG | GGCTGCCCCA | AAAGGAACTA | AAAGGGATCC | AGCTTTGAAT | 240 |
| TC | | | | | | 242 |

( 2 ) INFORMATION FOR SEQ ID NO:10:

( i ) SEQUENCE CHARACTERISTICS:
        ( A ) LENGTH: 341 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

| AACCAGCGTG | TTGAGCCTGA | ATGGTACATT | CCTATTATTC | CCATGGTGCT | GATAAATGGT | 60 |
| GCTGAAGGAA | TCGGTACTGG | GTGGTCCTGC | AAAATCCCCA | ACTTTGATGT | GCGTGAAATT | 120 |
| GTAAATAACA | TCAGGCGTTT | GATGGATGGA | GAAGAACCTT | TGCCAATGCT | TCCAAGTTAC | 180 |
| AAGAACTTCA | AGGGTACTAT | TGAAGAACTG | GCTCCAAATC | AATATGTGAT | TAGTGGTGAA | 240 |
| GTAGCTATTC | TTAATTCTAC | AACCATTGAA | ATCTCAGAGC | TTCCCGTCAG | AACATGGACC | 300 |
| CAGACATACA | AAGAACAAGT | TCTAGAACCC | ATGTTGAATG | G | | 341 |

( 2 ) INFORMATION FOR SEQ ID NO:11:

( i ) SEQUENCE CHARACTERISTICS:
        ( A ) LENGTH: 220 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:11:

| AATTCAAAGC | TGGATCCCTT | TTAGTTCCTT | TTGGGGCAGC | CCTTTTTTTG | GCACCGGTAG | 60 |
| TGGAGGTGGA | AGACTGACTT | TTTGCTGCTG | TCTTCTTCAC | TGTCACATTC | TTTTTAGGAA | 120 |
| CTGGGTTTGT | AATTTCAGTT | TCATCTGGGA | AATGTGTAGC | AGGAGGGCTT | GAAGACAGTG | 180 |
| GTACACTGCC | CTTAACATCA | TCAGCTTCAA | GGTCTGACAC | | | 220 |

( 2 ) INFORMATION FOR SEQ ID NO:12:

( i ) SEQUENCE CHARACTERISTICS:
        ( A ) LENGTH: 170 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

| GTGTTGAGCC | TGAATGGTAC | ATTCCTATTA | TTCCCATGGT | GCTGATAAAT | GGTGCTGAAG | 60 |
| GAATCGGTAC | TGGGTGGTCC | TGCAAAATCC | CCAACTTTGA | TGTGCGTGAA | ATTGTAAATA | 120 |
| ACATCAGGCG | TTTGATGGAT | GGAGAAGAAC | CTTTGCCAAT | GCTTCCAAGT | | 170 |

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

```
AATCATCGAT GGATGGATGG                                                                  20
```

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:14:

```
CCATCCATCCATCGATGATTAAA                                                                23
```

( 2 ) INFORMATION FOR SEQ ID NO:15:

( i ) SEQUENCE CHARACTERISTICS:
        ( A ) LENGTH: 327 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:15:

```
CTTGATCCCT  TCTGGTTGAT  GCCAGAAGCT  CTTCCTGATC  CAGCATTTGT  ATCTTCAATT    60
TCTCTACCAA  TTGGCTTTGT  TGGTTAATCT  CTTCATCCTT  GTCATCAAGT  TGTTTATACA   120
ATTTAGCAAG  TTCTTCTTCA  CACTTTCTTC  TTTCAGCATC  GGTAAAACTA  CCAGCCATTC   180
CGACTGCAGC  AGCTGGTTTA  TCACTGGTAA  TAGCAATATC  TTTATCCGCT  GTGAAGGCTT   240
CCAAATTAGC  TTTCTCTTTG  TCAAACTGCT  CATCAATAGG  CACTGTCTCC  CCGTTACGCC   300
AACGGTTTAG  CTCGTTTTCC  AGCCACT                                          327
```

( 2 ) INFORMATION FOR SEQ ID NO:16:

( i ) SEQUENCE CHARACTERISTICS:
        ( A ) LENGTH: 250 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:16:

| | | | | | |
|---|---|---|---|---|---|
| CCGACCGGGA | GCGGGAGAAG | GAGCGGGAGC | GGGAGCAGCG | GGAGAAGGAG | CGGGAGAAGG | 60
| AGCTGGAGCG | CGACGGGAGA | AGGAACGGGA | GCGCGAGCTG | GAGCGGCAGC | GGGAGCAGCG | 120
| GGCGAGGGAG | AAGGAGCTGC | TGGCTGCCAA | GGCCTTAGAG | CCCACCACCT | TCCTGCCTGT | 180
| GGCCGAGCTG | CACGGACTCC | GAGGTCACAG | CACGGAGGAG | CGGCCCAAGC | CCTCGGAGCA | 240
| GCTGACCCCA | | | | | | 250

( 2 ) INFORMATION FOR SEQ ID NO:17:

( i ) SEQUENCE CHARACTERISTICS:
        ( A ) LENGTH: 208 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:17:

| | | | | | |
|---|---|---|---|---|---|
| CTCAGAGGTG | ATCCTCTCGG | AGTCGAGCTC | AGGAGAAGGA | GTCCCCTTCT | TTGAGACTTG | 60
| GATGCAGACC | TGCATGTCCG | AGGAGGGCAA | GATTTGAAC | CCTGACCATC | CCTGCTTCCG | 120
| CCCTGACTCC | ACCGAAGTCG | AGTCCTTGGT | GGCCCTGCTC | AACAACTCTT | CAGAGATGAA | 180
| GCTAGTACAG | ATGAAGTAGC | ACGAGGCC | | | | 208

( 2 ) INFORMATION FOR SEQ ID NO:18:

( i ) SEQUENCE CHARACTERISTICS:
        ( A ) LENGTH: 2389 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:18:

| | | | | | |
|---|---|---|---|---|---|
| CGACAAACAT | CATCTGGGAA | GACCCACACG | ATGGAGGGTA | AACTTCATGA | TCCAGAAGGC | 60
| ATGGGAATTA | TTCCAAGAAT | AGTGCAAGAT | ATTTTAATT | ATATTTACTC | CATGGATGAA | 120
| AATTTGGAAT | TCATATTAA | GGTTTCATAT | TTGAAATAT | ATTTGGATAA | GATAAGGGAC | 180
| TTGTTAGATG | TTTCAAAGAC | TAACCTTTCA | GTCCATGAAG | ACAAAAACCG | TGTTCCCTAT | 240
| GTAAGGGGT | GCACAGAACG | TTTCGTGTGT | AGTCCAGATG | AAGTCATGGA | TACCATAGAT | 300
| GAAGGGAAAT | CCAACAGAGA | TGTCGCAGTT | ACAAATATGA | ATGAACATAG | CTCTAGGAGC | 360
| CACAGCATAT | TTCTTATTAA | TGTAAAACAA | GAGAATACAC | AAACGGAACA | GAAACTCAGT | 420
| GGAAAGCTTT | ATCTGGTTGA | TTTAGCTGGC | AGTGAGAAGG | TTAGTAAGAC | TGGGGCTGAA | 480
| GGTGCTGTGC | TGGATGAAGC | TAAGAACATC | AAGAAGTCAC | TTCTGCACT | TGGAAATGTC | 540
| ATTTCTGCTT | TGGCAGAGGG | CAGTACCTAT | GTTCCTTATC | GAGATAGTAA | AATGACCAGA | 600
| ATTCTTCAAG | ATTCATTAGG | TGGCAACTGT | AGGACCACTA | TTGTCATATG | CTGCTCTCCA | 660
| TCATCATACA | ATGAGTCTGA | GACAAAGTCA | ACACTCCTCT | TGGTCAAAG | GGCCAAAACA | 720
| ATTAAGAACA | CAGTCTGTGT | CAATGTAGAG | TTAACTGCAG | AGCAGTGGAA | AAAGAAGTAT | 780
| GAAAAAGAAA | AGGAAAAAAA | TAAGACTCTA | CGGAACACTA | TTCAGTGGCT | GGAAAACGAG | 840

```
CTAAACCGTT GGCGTAACGG GGAGACAGTG CCTATTGATG AGCAGTTTGA CAAAGAGAAA      900
GCTAATTTGG AAGCCTTCAC AGCGGATAAA GATACTGCTA TTACCAGTGA TAAACCAGCT      960
GCTGCAGTCG GAATGGCTGG TAGTTTTACC GATGCTGAAA GAAGAAAGTG TGAAGAAGAA     1020
CTTGCTAAAT TGTATAAACA GCTTGATGAC AAGGATGAAG AGATTAACCA ACAAAGCCAA     1080
TTGGTAGAGA AATTGAAGAC ACAAATGCTG GATCAGGAAG AGCTTCTGGC ATCAACCAGA     1140
AGGGATCAAG ATAATATGCA AGCTGAACTG AATCGCCTCC AAGCAGAAAA TGATGCTTCT     1200
AAAGAAGAAG TCAAAGAAGT TTTACAGGCC TTAGAGGAAC TGGCTGTTAA TTATGATCAG     1260
AAGTCTCAGG AAGTTGAAGA CAAAACAAAG GAATATGAAT TGCTTAGTGA TGAATTGAAT     1320
CAAAAATCTG CAACTTTAGC AAGTATTGAT GCTGAGCTTC AGAAGCTGAA GGAAATGACC     1380
AACCACCAGA AGAAACGAGC AGCTGAAATG ATGGCATCAT TATTAAAAGA CCTTGCAGAA     1440
ATAGGAATTG CTGTGGGGAA TAACGATGTG AAGCAACCAG AAGGAACTGG TATGATAGAT     1500
GAAGAGTTTA CTGTTGCAAG ACTCTACATT AGCAAAATGA ATCAGAAGT AAAGACCATG      1560
GTGAAACGCT GCAAACAGCT AGAAGCACG CAGACTGAGA GCAACAAAAA AATGGAAGAA      1620
AATGAGAAAG AGTTAGCAGC ATGCCAGCTT CGGATCTCCC AACATGAAGC CAAAATCAAG     1680
TCACTGACTG AGTACCTTCA GAATGTAGAA CAAAAGAAGA GGCAGCTGGA GGAATCTGTT     1740
GATTCCCTTG GTGAGGAGCT AGTCCAACTC GAGCACAAG AGAAAGTCCA TGAAATGGAA      1800
AAAGAGCACT TGAACAAGGT TCAGACTGCA AATGAAGTCA AGCAAGCTGT TGAGCAGCAG     1860
ATCCAGAGTC ACAGAGAAAC CCACCAAAAA CAAATCAGTA GCTTGCGAGA TGAAGTTGAG     1920
GCAAAGGAAA AGCTAATCAC TGACCTCCAA GACCAAAACC AGAAGATGGT GTTGGAGCAG     1980
GAACGGCTAA GGGTGGAGCA TGAGAGGCTG AAGGCTACAG ACCAAGAGAA GAGCAGGAAG     2040
CTGCATGAGC TCACGGTTAT GCAAGACAGA CGAGAACAAG CAAGACAAGA CTTGAAGGGT     2100
TTGGAGGAGA CCGTGGCAAA AGAACTTCAG ACTTTACACA ACCTGCGTAA GCTCTTTGTT     2160
CAGGACTTGG CTACCAGGGT GAAAAGAGG CCGAGGTCGA CTCTGACGAC ACTGGCGGCA      2220
GTGCTGCACA GAAGCAGAAA ATCTCCTTCC TTGAAAACAA CCTTGAACAG CTCACCAAAG     2280
TGCACAAGCA GTTGGTACGT GATAATGCAG ATCTTCGCTG TGAGCTTCCT AAGTTAGAGA     2340
AACGGCTTAG AGCTACTGCA GAAAGAGTGA AAGCTTTGGA GTCAGCCCG               2389
```

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:19:

```
AGTGGCTGGA AAACGAGCTA                                                   20
```

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:20:

CTTGATCCCT TCTGGTTGAT                      20

(2) INFORMATION FOR SEQ ID NO:21:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:21:

AGTGGCTTGA AAATGAGCTC                      20

(2) INFORMATION FOR SEQ ID NO:22:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:22:

CTTGATCCCT TCTGGTAGAT G                    21